United States Patent
Guo et al.

(10) Patent No.: US 12,089,953 B1
(45) Date of Patent: Sep. 17, 2024

(54) SYSTEMS AND METHODS FOR UTILIZING INTRINSIC CURRENT NOISE TO MEASURE INTERFACE IMPEDANCES

(71) Applicant: META PLATFORMS TECHNOLOGIES, LLC, Menlo Park, CA (US)

(72) Inventors: Ning Guo, New York, NY (US); Jonathan Reid, San Jose, CA (US)

(73) Assignee: META PLATFORMS TECHNOLOGIES, LLC, Menlo Park, CA (US)

(*) Notice: Subject to any disclaimer, the term of this patent is extended or adjusted under 35 U.S.C. 154(b) by 712 days.

(21) Appl. No.: 17/112,629

(22) Filed: Dec. 4, 2020

Related U.S. Application Data

(60) Provisional application No. 62/943,669, filed on Dec. 4, 2019.

(51) Int. Cl.
| | |
|---|---|
| *G06F 3/01* | (2006.01) |
| *A61B 5/00* | (2006.01) |
| *A61B 5/313* | (2021.01) |
| *G01R 27/26* | (2006.01) |
| *G01R 29/26* | (2006.01) |

(52) U.S. Cl.
CPC ............ *A61B 5/6843* (2013.01); *A61B 5/313* (2021.01); *A61B 5/7221* (2013.01); *G01R 27/26* (2013.01); *G01R 29/26* (2013.01); *G06F 3/015* (2013.01); *A61B 2560/0209* (2013.01)

(58) Field of Classification Search
None
See application file for complete search history.

(56) References Cited

U.S. PATENT DOCUMENTS

| | | | |
|---|---|---|---|
| 4,055,168 | A | 10/1977 | Miller et al. |
| 4,896,120 | A | 1/1990 | Kamil |
| 5,625,577 | A | 4/1997 | Kunii et al. |
| (Continued) | | | |

FOREIGN PATENT DOCUMENTS

| | | |
|---|---|---|
| CA | 2902045 A1 | 8/2014 |
| CA | 2921954 A1 | 2/2015 |
| (Continued) | | |

OTHER PUBLICATIONS

Arkenbout et al., Robust Hand Motion Tracking through Data Fusion of 5DT Data Glove and Nimble VR Kinect Camera Measurements. Sensors. 2015;15:31644-71.
(Continued)

*Primary Examiner* — Carl Adams
(74) *Attorney, Agent, or Firm* — Morgan, Lewis & Bockius LLP

(57) ABSTRACT

The disclosed computer-implemented method may include (1) sampling an output signal of an amplifier that amplifies a voltage difference between two electrodes, (2) calculating, based on a power spectral density of the output signal, a noise power of the output signal over a predetermined frequency band, (3) estimating an interface impedance of at least one of the two electrodes based on the noise power and a predetermined intrinsic current noise of the amplifier, and (4) performing an operation based at least in part on the estimated interface impedance. Various other methods, systems, and devices are also disclosed.

20 Claims, 16 Drawing Sheets

(56) References Cited

U.S. PATENT DOCUMENTS

| | | |
|---|---|---|
| 6,005,548 A | 12/1999 | Latypov et al. |
| 6,009,210 A | 12/1999 | Kand |
| 6,244,873 B1 | 6/2001 | Hill et al. |
| 6,411,843 B1 | 6/2002 | Zarychta |
| 6,658,287 B1 | 12/2003 | Litt et al. |
| 6,720,984 B1 | 4/2004 | Jorgensen et al. |
| 6,774,885 B1 | 8/2004 | Even-Zohar |
| 6,942,621 B2 | 9/2005 | Avinash et al. |
| 7,089,148 B1 | 8/2006 | Bachmann et al. |
| 7,351,975 B2 | 4/2008 | Brady et al. |
| 7,574,253 B2 | 8/2009 | Edney et al. |
| 7,580,742 B2 | 8/2009 | Tan et al. |
| 7,787,946 B2 | 8/2010 | Stahmann et al. |
| 7,805,386 B2 | 9/2010 | Greer |
| 7,901,368 B2 | 3/2011 | Flaherty et al. |
| 8,170,656 B2 | 5/2012 | Tan et al. |
| 8,190,249 B1 | 5/2012 | Gharieb et al. |
| 8,311,623 B2 | 11/2012 | Sanger |
| 8,351,651 B2 | 1/2013 | Lee |
| 8,421,634 B2 | 4/2013 | Tan et al. |
| 8,435,191 B2 | 5/2013 | Barboutis et al. |
| 8,437,844 B2 | 5/2013 | Syed Momen et al. |
| 8,447,704 B2 | 5/2013 | Tan et al. |
| 8,484,022 B1 | 7/2013 | Vanhoucke |
| 8,718,980 B2 | 5/2014 | Garudadri et al. |
| 8,744,543 B2 | 6/2014 | Li et al. |
| 8,754,862 B2 | 6/2014 | Zaliva |
| D717,685 S | 11/2014 | Bailey et al. |
| 8,880,163 B2 | 11/2014 | Barachant et al. |
| 8,890,875 B2 | 11/2014 | Jammes et al. |
| 8,892,479 B2 | 11/2014 | Tan et al. |
| 9,037,530 B2 | 5/2015 | Tan et al. |
| D742,272 S | 11/2015 | Bailey et al. |
| 9,218,574 B2 | 12/2015 | Phillipps et al. |
| 9,235,934 B2 | 1/2016 | Mandella et al. |
| 9,240,069 B1 | 1/2016 | Li |
| 9,278,453 B2 | 3/2016 | Assad |
| 9,299,248 B2 | 3/2016 | Lake et al. |
| D756,359 S | 5/2016 | Bailey et al. |
| 9,351,653 B1 | 5/2016 | Harrison |
| 9,367,139 B2 | 6/2016 | Ataee et al. |
| 9,372,535 B2 | 6/2016 | Bailey et al. |
| 9,389,694 B2 | 7/2016 | Ataee et al. |
| 9,408,316 B2 | 8/2016 | Bailey et al. |
| 9,459,697 B2 | 10/2016 | Bedikian et al. |
| 9,483,123 B2 | 11/2016 | Aleem et al. |
| 9,597,015 B2 | 3/2017 | McNames et al. |
| 9,600,030 B2 | 3/2017 | Bailey et al. |
| 9,612,661 B2 | 4/2017 | Wagner et al. |
| 9,613,262 B2 | 4/2017 | Holz |
| 9,654,477 B1 | 5/2017 | Kotamraju |
| 9,659,403 B1 | 5/2017 | Horowitz |
| 9,687,168 B2 | 6/2017 | John |
| 9,696,795 B2 | 7/2017 | Marcolina et al. |
| 9,720,515 B2 | 8/2017 | Wagner et al. |
| 9,741,169 B1 | 8/2017 | Holz |
| 9,766,709 B2 | 9/2017 | Holz |
| 9,785,247 B1 | 10/2017 | Horowitz et al. |
| 9,788,789 B2 | 10/2017 | Bailey |
| 9,864,431 B2 | 1/2018 | Keskin et al. |
| 9,867,548 B2 | 1/2018 | Le et al. |
| 9,880,632 B2 | 1/2018 | Ataee et al. |
| 9,891,718 B2 | 2/2018 | Connor |
| 10,042,422 B2 | 8/2018 | Morun et al. |
| 10,070,799 B2 | 9/2018 | Ang et al. |
| 10,078,435 B2 | 9/2018 | Noel |
| 10,101,809 B2 | 10/2018 | Morun et al. |
| 10,152,082 B2 | 12/2018 | Bailey |
| 10,188,309 B2 | 1/2019 | Morun et al. |
| 10,199,008 B2 | 2/2019 | Aleem et al. |
| 10,203,751 B2 | 2/2019 | Keskin et al. |
| 10,216,274 B2 | 2/2019 | Chapeskie et al. |
| 10,251,577 B2 | 4/2019 | Morun et al. |
| 10,310,601 B2 | 6/2019 | Morun et al. |
| 10,331,210 B2 | 6/2019 | Morun et al. |
| 10,362,958 B2 | 7/2019 | Morun et al. |
| 10,409,371 B2 | 9/2019 | Kaifosh et al. |
| 10,437,335 B2 | 10/2019 | Daniels |
| 10,460,455 B2 | 10/2019 | Giurgica-Tiron et al. |
| 10,489,986 B2 | 11/2019 | Kaifosh et al. |
| 10,496,168 B2 | 12/2019 | Kaifosh et al. |
| 10,504,286 B2 | 12/2019 | Kaifosh et al. |
| 2003/0144829 A1 | 7/2003 | Geatz et al. |
| 2003/0171921 A1 | 9/2003 | Manabe et al. |
| 2003/0184544 A1 | 10/2003 | Prudent |
| 2004/0092839 A1 | 5/2004 | Shin et al. |
| 2006/0129057 A1 | 6/2006 | Maekawa et al. |
| 2007/0009151 A1 | 1/2007 | Pittman et al. |
| 2007/0172797 A1 | 7/2007 | Hada et al. |
| 2007/0177770 A1 | 8/2007 | Derchak et al. |
| 2007/0256494 A1 | 11/2007 | Nakamura et al. |
| 2007/0285399 A1 | 12/2007 | Lund |
| 2008/0051673 A1 | 2/2008 | Kong et al. |
| 2008/0052643 A1 | 2/2008 | Ike et al. |
| 2008/0103639 A1 | 5/2008 | Troy et al. |
| 2008/0214360 A1 | 9/2008 | Stirling et al. |
| 2008/0221487 A1 | 9/2008 | Zohar et al. |
| 2009/0027337 A1 | 1/2009 | Hildreth |
| 2009/0079813 A1 | 3/2009 | Hildreth |
| 2009/0082692 A1 | 3/2009 | Hale et al. |
| 2009/0082701 A1 | 3/2009 | Zohar et al. |
| 2009/0112080 A1 | 4/2009 | Matthews |
| 2009/0124881 A1 | 5/2009 | Rytky |
| 2009/0326406 A1 | 12/2009 | Tan et al. |
| 2009/0327171 A1 | 12/2009 | Tan et al. |
| 2010/0030532 A1 | 2/2010 | Arora et al. |
| 2010/0063794 A1 | 3/2010 | Hernandez-Rebollar |
| 2010/0106044 A1 | 4/2010 | Linderman |
| 2010/0113910 A1 | 5/2010 | Brauers et al. |
| 2010/0280628 A1 | 11/2010 | Sankai |
| 2010/0292606 A1 | 11/2010 | Prakash et al. |
| 2010/0292617 A1 | 11/2010 | Lei et al. |
| 2010/0293115 A1 | 11/2010 | Seyed Momen |
| 2010/0315266 A1 | 12/2010 | Gunawardana et al. |
| 2011/0077484 A1 | 3/2011 | Van Slyke et al. |
| 2011/0092826 A1 | 4/2011 | Lee et al. |
| 2011/0173204 A1 | 7/2011 | Murillo et al. |
| 2011/0173574 A1 | 7/2011 | Clavin et al. |
| 2011/0230782 A1 | 9/2011 | Bartol et al. |
| 2012/0066163 A1 | 3/2012 | Balls et al. |
| 2012/0188158 A1 | 7/2012 | Tan et al. |
| 2012/0265480 A1 | 10/2012 | Oshima |
| 2012/0283526 A1 | 11/2012 | Gommesen et al. |
| 2013/0004033 A1 | 1/2013 | Trugenberger |
| 2013/0077820 A1 | 3/2013 | Marais et al. |
| 2013/0123656 A1 | 5/2013 | Heck |
| 2013/0141375 A1 | 6/2013 | Ludwig et al. |
| 2013/0207889 A1 | 8/2013 | Chang et al. |
| 2013/0217998 A1 | 8/2013 | Mahfouz et al. |
| 2013/0232095 A1 | 9/2013 | Tan et al. |
| 2013/0317382 A1 | 11/2013 | Le |
| 2013/0317648 A1 | 11/2013 | Assad |
| 2014/0052150 A1 | 2/2014 | Taylor et al. |
| 2014/0092009 A1 | 4/2014 | Yen et al. |
| 2014/0098018 A1 | 4/2014 | Kim et al. |
| 2014/0196131 A1 | 7/2014 | Lee |
| 2014/0198034 A1 | 7/2014 | Bailey et al. |
| 2014/0198035 A1 | 7/2014 | Bailey et al. |
| 2014/0223462 A1 | 8/2014 | Aimone et al. |
| 2014/0240103 A1 | 8/2014 | Lake et al. |
| 2014/0240223 A1 | 8/2014 | Lake et al. |
| 2014/0245200 A1 | 8/2014 | Holz |
| 2014/0249397 A1 | 9/2014 | Lake et al. |
| 2014/0277622 A1 | 9/2014 | Raniere |
| 2014/0278441 A1 | 9/2014 | Ton et al. |
| 2014/0297528 A1 | 10/2014 | Agrawal et al. |
| 2014/0304665 A1 | 10/2014 | Holz |
| 2014/0330404 A1 | 11/2014 | Abdelghani et al. |
| 2014/0334083 A1 | 11/2014 | Bailey |
| 2014/0344731 A1 | 11/2014 | Holz |
| 2014/0355825 A1 | 12/2014 | Kim et al. |
| 2014/0358024 A1 | 12/2014 | Nelson et al. |
| 2014/0361988 A1 | 12/2014 | Katz et al. |
| 2014/0364703 A1 | 12/2014 | Kim et al. |

(56) References Cited

U.S. PATENT DOCUMENTS

| | | |
|---|---|---|
| 2014/0365163 A1 | 12/2014 | Jallon |
| 2014/0376773 A1 | 12/2014 | Holz |
| 2015/0006120 A1 | 1/2015 | Sett et al. |
| 2015/0010203 A1 | 1/2015 | Muninder et al. |
| 2015/0025355 A1 | 1/2015 | Bailey et al. |
| 2015/0029092 A1 | 1/2015 | Holz et al. |
| 2015/0035827 A1 | 2/2015 | Yamaoka et al. |
| 2015/0045689 A1 | 2/2015 | Barone |
| 2015/0045699 A1 | 2/2015 | Mokaya et al. |
| 2015/0051470 A1 | 2/2015 | Bailey et al. |
| 2015/0057770 A1 | 2/2015 | Bailey et al. |
| 2015/0070270 A1 | 3/2015 | Bailey et al. |
| 2015/0070274 A1 | 3/2015 | Morozov |
| 2015/0084860 A1 | 3/2015 | Aleem et al. |
| 2015/0109202 A1 | 4/2015 | Ataee et al. |
| 2015/0124566 A1 | 5/2015 | Lake et al. |
| 2015/0128094 A1 | 5/2015 | Baldwin et al. |
| 2015/0141784 A1 | 5/2015 | Morun et al. |
| 2015/0148641 A1 | 5/2015 | Morun et al. |
| 2015/0157944 A1 | 6/2015 | Gottlieb |
| 2015/0169074 A1 | 6/2015 | Ataee et al. |
| 2015/0193949 A1 | 7/2015 | Katz et al. |
| 2015/0223716 A1 | 8/2015 | Korkala et al. |
| 2015/0234426 A1 | 8/2015 | Bailey et al. |
| 2015/0261306 A1 | 9/2015 | Lake |
| 2015/0261318 A1 | 9/2015 | Scavezze et al. |
| 2015/0277575 A1 | 10/2015 | Ataee et al. |
| 2015/0296553 A1 | 10/2015 | DiFranco et al. |
| 2015/0302168 A1 | 10/2015 | De Sapio et al. |
| 2015/0306373 A1* | 10/2015 | Bouton .................. G06F 3/015 607/148 |
| 2015/0309563 A1 | 10/2015 | Connor |
| 2015/0309582 A1 | 10/2015 | Gupta |
| 2015/0313496 A1 | 11/2015 | Connor |
| 2015/0325202 A1 | 11/2015 | Lake et al. |
| 2015/0332013 A1 | 11/2015 | Lee et al. |
| 2015/0346701 A1 | 12/2015 | Gordon et al. |
| 2015/0366504 A1 | 12/2015 | Connor |
| 2015/0370326 A1 | 12/2015 | Chapeskie et al. |
| 2015/0370333 A1 | 12/2015 | Ataee et al. |
| 2016/0011668 A1 | 1/2016 | Gilad-Bachrach et al. |
| 2016/0049073 A1 | 2/2016 | Lee |
| 2016/0092504 A1 | 3/2016 | Mitri et al. |
| 2016/0144172 A1 | 5/2016 | Hsueh et al. |
| 2016/0162604 A1 | 6/2016 | Xioli et al. |
| 2016/0187992 A1 | 6/2016 | Yamamoto et al. |
| 2016/0235323 A1 | 8/2016 | Tadi et al. |
| 2016/0239080 A1 | 8/2016 | Marcolina et al. |
| 2016/0262687 A1 | 9/2016 | Imperial |
| 2016/0274758 A1 | 9/2016 | Bailey |
| 2016/0275726 A1 | 9/2016 | Mullins |
| 2016/0292497 A1 | 10/2016 | Kehtarnavaz et al. |
| 2016/0313798 A1 | 10/2016 | Connor |
| 2016/0313801 A1 | 10/2016 | Wagner et al. |
| 2016/0313890 A1 | 10/2016 | Walline et al. |
| 2016/0313899 A1 | 10/2016 | Noel |
| 2016/0350973 A1 | 12/2016 | Shapira et al. |
| 2017/0031502 A1 | 2/2017 | Rosenberg et al. |
| 2017/0035313 A1 | 2/2017 | Hong et al. |
| 2017/0061817 A1 | 3/2017 | Mettler May |
| 2017/0068445 A1 | 3/2017 | Lee et al. |
| 2017/0080346 A1 | 3/2017 | Abbas |
| 2017/0090604 A1 | 3/2017 | Barbier |
| 2017/0091567 A1 | 3/2017 | Wang et al. |
| 2017/0119472 A1 | 5/2017 | Herrmann et al. |
| 2017/0123487 A1 | 5/2017 | Hazra et al. |
| 2017/0124816 A1 | 5/2017 | Yang et al. |
| 2017/0161635 A1 | 6/2017 | Oono et al. |
| 2017/0188980 A1 | 7/2017 | Ash |
| 2017/0259167 A1 | 9/2017 | Cook et al. |
| 2017/0285756 A1 | 10/2017 | Wang et al. |
| 2017/0285848 A1 | 10/2017 | Rosenberg et al. |
| 2017/0296363 A1 | 10/2017 | Yetkin et al. |
| 2017/0301630 A1 | 10/2017 | Nguyen et al. |
| 2017/0308118 A1 | 10/2017 | Ito |
| 2017/0344706 A1 | 11/2017 | Tones et al. |
| 2017/0347908 A1 | 12/2017 | Watanabe et al. |
| 2018/0000367 A1 | 1/2018 | Longinotti-Buitoni |
| 2018/0020951 A1 | 1/2018 | Kaifosh et al. |
| 2018/0020978 A1 | 1/2018 | Kaifosh et al. |
| 2018/0024634 A1 | 1/2018 | Kaifosh et al. |
| 2018/0024635 A1 | 1/2018 | Kaifosh et al. |
| 2018/0064363 A1 | 3/2018 | Morun et al. |
| 2018/0067553 A1 | 3/2018 | Morun et al. |
| 2018/0081439 A1 | 3/2018 | Daniels |
| 2018/0088765 A1 | 3/2018 | Bailey |
| 2018/0095630 A1 | 4/2018 | Bailey |
| 2018/0101235 A1 | 4/2018 | Bodensteiner et al. |
| 2018/0101289 A1 | 4/2018 | Bailey |
| 2018/0120948 A1 | 5/2018 | Aleem et al. |
| 2018/0140441 A1 | 5/2018 | Poirters |
| 2018/0150033 A1 | 5/2018 | Lake et al. |
| 2018/0153430 A1 | 6/2018 | Ang et al. |
| 2018/0153444 A1 | 6/2018 | Yang et al. |
| 2018/0154140 A1 | 6/2018 | Bouton et al. |
| 2018/0178008 A1 | 6/2018 | Bouton et al. |
| 2018/0301057 A1 | 10/2018 | Hargrove et al. |
| 2018/0307314 A1 | 10/2018 | Connor |
| 2018/0321745 A1 | 11/2018 | Morun et al. |
| 2018/0321746 A1 | 11/2018 | Morun et al. |
| 2018/0333575 A1 | 11/2018 | Bouton |
| 2018/0344195 A1 | 12/2018 | Morun et al. |
| 2018/0360379 A1 | 12/2018 | Harrison et al. |
| 2019/0008453 A1 | 1/2019 | Spoof |
| 2019/0025919 A1 | 1/2019 | Tadi et al. |
| 2019/0033967 A1 | 1/2019 | Morun et al. |
| 2019/0033974 A1 | 1/2019 | Mu et al. |
| 2019/0038166 A1 | 2/2019 | Tavabi et al. |
| 2019/0076716 A1 | 3/2019 | Chiou et al. |
| 2019/0121305 A1 | 4/2019 | Kaifosh et al. |
| 2019/0121306 A1 | 4/2019 | Kaifosh et al. |
| 2019/0146809 A1 | 5/2019 | Lee et al. |
| 2019/0150777 A1 | 5/2019 | Guo et al. |
| 2019/0192037 A1 | 6/2019 | Morun et al. |
| 2019/0212817 A1 | 7/2019 | Kaifosh et al. |
| 2019/0223748 A1 | 7/2019 | Al-Natsheh et al. |
| 2019/0227627 A1 | 7/2019 | Kaifosh et al. |
| 2019/0228330 A1 | 7/2019 | Kaifosh et al. |
| 2019/0228533 A1 | 7/2019 | Giurgica-Tiron et al. |
| 2019/0228579 A1 | 7/2019 | Kaifosh et al. |
| 2019/0228590 A1 | 7/2019 | Kaifosh et al. |
| 2019/0228591 A1 | 7/2019 | Giurgica-Tiron et al. |
| 2019/0231204 A1* | 8/2019 | Heydari ............... A61B 5/6868 |
| 2019/0247650 A1 | 8/2019 | Tran |
| 2019/0324549 A1 | 10/2019 | Araki et al. |
| 2019/0357787 A1 | 11/2019 | Barachant et al. |
| 2019/0362557 A1 | 11/2019 | Lacey et al. |

FOREIGN PATENT DOCUMENTS

| | | |
|---|---|---|
| CA | 2939644 A1 | 8/2015 |
| CN | 1838933 A | 9/2006 |
| CN | 103777752 A | 5/2014 |
| CN | 105190578 A | 12/2015 |
| CN | 106102504 A | 11/2016 |
| EP | 1838933 A | 9/2006 |
| EP | 2198521 B1 | 6/2012 |
| EP | 2959394 A1 | 12/2015 |
| EP | 3104737 A1 | 12/2016 |
| JP | H05-277080 A | 10/1993 |
| JP | 2005-095561 A | 4/2005 |
| JP | 2010-520561 A | 6/2010 |
| JP | 2016-507851 A | 3/2016 |
| JP | 2017-509386 A | 4/2017 |
| KR | 2015-0123254 A | 11/2015 |
| KR | 2016-0121552 A | 10/2016 |
| KR | 10-1790147 B1 | 10/2017 |
| WO | 2008/109248 A2 | 9/2008 |
| WO | 2009/042313 A1 | 4/2009 |
| WO | 2010/104879 A2 | 9/2010 |
| WO | 2012/155157 | 11/2012 |
| WO | 2014/130871 A1 | 8/2014 |
| WO | 2014/186370 A1 | 11/2014 |
| WO | 2014/194257 A1 | 12/2014 |

(56) References Cited

FOREIGN PATENT DOCUMENTS

| WO | 2014/197443 | A1 | 12/2014 |
|---|---|---|---|
| WO | 2015/027089 | A1 | 2/2015 |
| WO | 2015/073713 | A1 | 5/2015 |
| WO | 2015/081113 | A1 | 6/2015 |
| WO | 2015/123445 | A1 | 8/2015 |
| WO | 2015/199747 | A1 | 12/2015 |
| WO | 2016/041088 | | 3/2016 |
| WO | 2016/041088 | A1 | 3/2016 |
| WO | 2017/062544 | | 4/2017 |
| WO | 2017/092225 | A1 | 6/2017 |
| WO | 2017/120669 | | 7/2017 |
| WO | 2017/172185 | A1 | 10/2017 |
| WO | 2017/208167 | A1 | 12/2017 |

OTHER PUBLICATIONS

Benko et al., Enhancing Input On and Above the Interactive Surface with Muscle Sensing. The ACM International Conference on Interactive Tabletops and Surfaces. ITS '09. 2009:93-100.

Boyali et al., Spectral Collaborative Representation based Classification for hand gestures recognition on electromyography signals. Biomedical Signal Processing and Control. 2016;24:1118.

Cheng et al., A Novel Phonology- and Radical-Coded Chinese Sign Language Recognition Framework Using Accelerometer and Surface Electromyography Sensors. Sensors. 2015;15:23303-24.

Csapo et al., Evaluation of Human-Myo Gesture Control Capabilities in Continuous Search and Select Operations. 7th IEEE International Conference on Cognitive Infocommunications. 2016;000415-20.

Davoodi et al., Development of a Physics-Based Target Shooting Game to Train Amputee Users of Multijoint Upper Limb Prostheses. Presence. Massachusetts Institute of Technology. 2012;21(1):85-95.

Delis et al., Development of a Myoelectric Controller Based on Knee Angle Estimation. Biodevices 2009. International Conference on Biomedical Electronics and Devices. Jan. 17, 2009. 7 pages.

Diener et al., Direct conversion from facial myoelectric signals to speech using Deep Neural Networks. 2015 International Joint Conference on Neural Networks (IJCNN). Oct. 1, 2015. 7 pages.

Ding et al., HMM with improved feature extraction-based feature parameters for identity recognition of gesture command operators by using a sensed Kinect-data stream. Neurocomputing. 2017;262:108-19.

Farina et al., Man/machine interface based on the discharge timings of spinal motor neurons after targeted muscle reinnervation. Nature. Biomedical Engineering. 2017;1:1-12.

Favorskaya et al., Localization and Recognition of Dynamic Hand Gestures Based on Hierarchy of Manifold Classifiers. International Archives of the Photogrammetry, Remote Sensing and Spatial Information Sciences. 2015;XL-5/W6:1-8.

Gallina et al., Surface EMG Biofeedback. Surface Electromyography: Physiology, Engineering, and Applications. 2016:485-500.

Gopura et al., A Human Forearm and wrist motion assist exoskeleton robot with EMG-based fuzzy-neuro control. Proceedings of the 2nd IEEE/RAS-EMBS International Conference on Biomedical Robotics and Biomechatronics. Oct. 19-22, 2008. 6 pages.

Hauschild et al., A Virtual Reality Environment for Designing and Fitting Neural Prosthetic Limbs. IEEE Transactions on Neural Systems and Rehabilitation Engineering. 2007;15(1):9-15.

Jiang, Purdue University Graduate School Thesis/Dissertation Acceptance. Graduate School Form 30. Updated Jan. 15, 2015. 24 pages.

Kawaguchi et al., Estimation of Finger Joint Angles Based on Electromechanical Sensing of Wrist Shape. IEEE Transactions on Neural Systems and Rehabilitation Engineering. 2017;25(9):1409-18.

Kim et al., Real-Time Human Pose Estimation and Gesture Recognition from Depth Images Using Superpixels and SVM Classifier. Sensors. 2015;15:12410-27.

Koerner, Design and Characterization of the Exo-Skin Haptic Device: A Novel Tendon Actuated Textile Hand Exoskeleton. 2017. 5 pages.

Lee et al., Motion and Force Estimation System of Human Fingers. Journal of Institute of Control, Robotics and Systems. 2011;17(10):1014-1020.

Li et al., Motor Function Evaluation of Hemiplegic Upper-Extremities Using Data Fusion from Wearable Inertial and Surface EMG Sensors. Sensors. MDPI. 2017;17(582):1-17.

Lopes et al., Hand/arm gesture segmentation by motion using IMU and EMG sensing. ScienceDirect. Elsevier. Procedia Manufacturing. 2017;11:107-13.

Martin et al., A Novel Approach of Prosthetic Arm Control using Computer Vision, Biosignals, and Motion Capture. IEEE. 2014. 5 pages.

Mcintee, A Task Model of Free-Space Movement-Based Gestures. Dissertation. Graduate Faculty of North Carolina State University. Computer Science. 2016. 129 pages.

Mendes et al., Sensor Fusion and Smart Sensor in Sports and Biomedical Applications. Sensors. 2016;16(1569):1-31.

Mohamed, Homogeneous cognitive based biometrics for static authentication. Dissertation submitted to University of Victoria, Canada. 2010. 149 pages. URL:http://hdl.h .net/1828/3211 [last accessed Oct. 11, 2019].

Naik et al., Source Separation and Identification issues in bio signals: A solution using Blind source separation. Intech. 2009. 23 pages.

Naik et al., Subtle Hand gesture identification for HCI using Temporal Decorrelation Source Separation BSS of surface EMG. Digital Image Computing Techniques and Applications. IEEE Computer Society. 2007;30-7.

Negro et al., Multi-channel intramuscular and surface EMG decomposition by convolutive blind source separation. Journal of Neural Engineering. 2016;13:1-17.

Saponas et al., Demonstrating the Feasibility of Using Forearm Electromyography for Muscle- Computer Interfaces. CHI 2008 Proceedings. Physiological Sensing for Input. 2008:515-24.

Saponas et al., Enabling Always-Available Input with Muscle-Computer Interfaces. UIST '09. 2009:167-76.

Saponas et al., Making Muscle-Computer Interfaces More Practical. CHI 2010: Brauns and Brawn. 2010:851-4.

Sartori et al., Neural Data-Driven Musculoskeletal Modeling for Personalized Neurorehabilitation Technologies. IEEE Transactions on Biomedical Engineering. 2016;63(5):879-93.

Sauras-Perez et al., A Voice and Pointing Gesture Interaction System for Supporting Human Spontaneous Decisions in Autonomous Cars. Clemson University. All Dissertations. 2017. 174 pages.

Shen et al., I am a Smartwatch and I can Track my User's Arm. University of Illinois at Urbana- Champaign. MobiSys' 16. 12 pages.

Son et al., Evaluating the utility of two gestural discomfort evaluation methods. PLOS One. 2017. 21 pages.

Strbac et al., Microsoft Kinect-Based Artificial Perception System for Control of Functional Electrical Stimulation Assisted Grasping. Hindawi Publishing Corporation. BioMed Research International. 2014. 13 pages.

Torres, Myo Gesture Control Armband. PCMag. Https://www.pom 18.001 rticle2/0.2817.2485462.00 asp 2015. 9 pages.

Valero-Cuevas et al., Computational Models for Neuromuscular Function. NIH Public Access Author Manuscript. Jun. 16, 2011. 52 pages.

Wodzinski et al., Sequential Classification of Palm Gestures Based on A* Algorithm and MLP Neural Network for Quadrocopter Control. Metrol. Meas. Syst., 2017;24(2):265-76.

Xue et al., Multiple Sensors Based Hand Motion Recognition Using Adaptive Directed Acyclic Graph. Applied Sciences. MDPI. 2017;7(358):1-14.

Yang et al., Surface EMG based handgrip force predictions using gene expression programming. Neurocomputing. 2016;207:568-579.

Al-Mashhadany, Inverse Kinematics Problem (IKP) of 6-DOF Manipulator Bgy Locally Recurrent Neural Networks (LRNNs).

(56) References Cited

OTHER PUBLICATIONS

Management and Service Science (MASS). 2010 International Conference On, IEEE. Aug. 24, 2010. 5 pages. ISBN: 978-1-4244-5325-2.

Kipke et al., Silicon-substrate Intracortical Microelectrode Arrays for Long-Term Recording of Neuronal Spike Activity in Cerebral Cortex. IEEE Transactions on Neural Systems and Rehabilitation Engineering. 2003; 11(2): 151-155.

Marcard et al., Sparse Inertial Poser: Automatic 3D Human Pose Estimation from Sparse IMUs. Eurographics. 2017;36(2). 12 pages.

Wittevrongel et al., Spatiotemporal Beamforming: A Transparent and Unified Decoding Approach to Synchronous Visual Brain-Computer Interfacing. Frontiers in Neuroscience. 2017;11:1-12.

Zacharaki et al., Spike pattern recognition by supervised classification in low dimensional embedding space. Brain Informatics. 2016;3:73-8. DOI: 10.1007/s40708-016-0044-4.

* cited by examiner

SYSTEMS AND METHODS FOR UTILIZING INTRINSIC CURRENT NOISE TO MEASURE INTERFACE IMPEDANCES

CROSS REFERENCE TO RELATED APPLICATION

This application claims the benefit of U.S. Provisional Application No. 62/943,669, filed 4 Dec. 2019, the disclosure of which is incorporated, in its entirety, by this reference.

BRIEF DESCRIPTION OF THE DRAWINGS

The accompanying drawings illustrate a number of exemplary embodiments and are a part of the specification. Together with the following description, these drawings demonstrate and explain various principles of the present disclosure.

Figure 1:
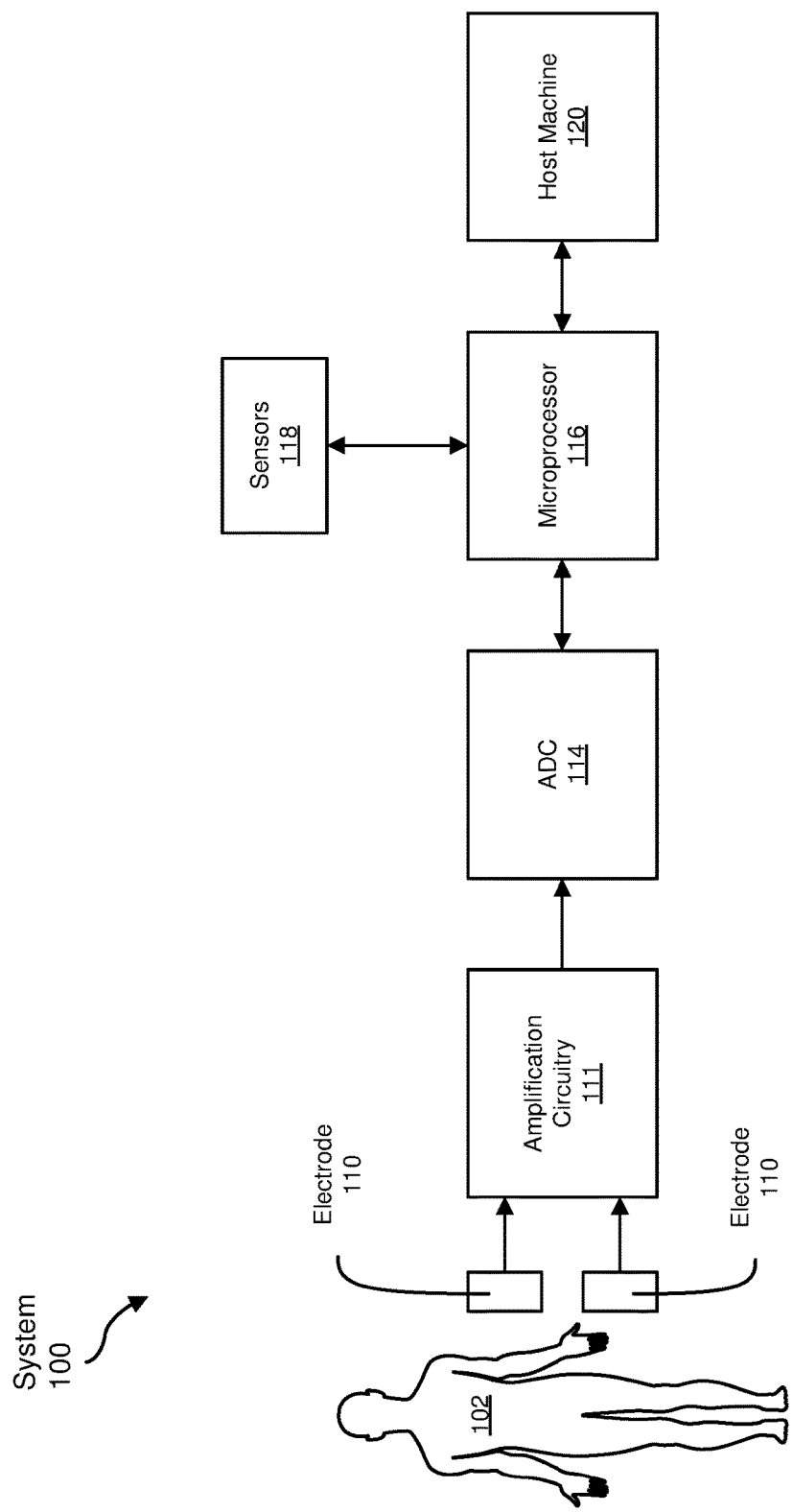
FIG. 1 is a schematic diagram of components of an exemplary biosignal sensing system in accordance with some embodiments of the technology described herein.

Throughout the drawings, identical reference characters and descriptions indicate similar, but not necessarily identical, elements. While the exemplary embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the present disclosure covers all modifications, equivalents, and alternatives falling within the scope of the appended claims.

DETAILED DESCRIPTION OF EXEMPLARY EMBODIMENTS

Biopotential sensors mounted on wearable devices are subjected to a number of conditions that may affect the quality of sensed signals. For instance, in the case of some neuromuscular sensors, sensed signals can be distorted by, for example, imperfect contact between sensors (e.g., electrodes) and skin. For some applications, high-fidelity neuromuscular sensor data may be desirable. For example, in an extended reality (XR) context (e.g., with virtual reality (VR) systems, augmented reality (AR) systems, and/or mixed reality systems), applications that use neuromuscular data to generate visualizations of a user's hand in real time or that use neuromuscular data to provide gesture-based input may rely on high-fidelity data in order to improve a user's sense of immersion and/or overall experience.

Surface electromyography (sEMG) involves the detection of electrical activity produced by one or more groups of muscles, at rest and/or during activity. High quality sEMG signals have conventionally been acquired from wet electrodes in a laboratory setting using skin preparations that require application of a gel or paste at the electrode-skin interface to improve conductivity between the skin and the electrodes. Obtaining consistently high-quality neuromuscular (e.g., sEMG) signals using electrodes and conventional signal conditioning and processing techniques is challenging, in part due to the low voltages produced by muscle fibers. Moreover, obtaining high-quality neuromuscular signals from dry electrodes may be more challenging than with so-called wet electrodes, because wet electrodes generally have a more direct conductive path between the electrode and the skin via an intervening gel. With dry electrodes, however, there may be various low conductivity materials between the electrodes and the skin, such as air gaps, body hair, and/or dust, resulting in inconsistent electrode signals that may exhibit considerable noise. For applications that require near real-time analysis of neuromuscular signals with dry electrodes, the acquisition of consistently high-quality signals with reliable devices is important.

When dry electrodes are used, recorded neuromuscular signals may exhibit more noise than wet electrodes due, in part, to their higher interface impedance. As discussed above, some conventional neuromuscular activity detection techniques employ so-called wet electrodes to which a conductive gel and/or paste is applied to lower the interface impedance between the electrodes and the skin. In contrast, dry electrodes, which do not use gels or pastes, generally have a higher impedance at the electrode-skin interface. Higher amounts of impedance at the electrode-skin interface (e.g., created when a user has hairy skin on which the electrodes are placed) may result in exacerbation of intrinsic and extrinsic noise phenomenon. It would be advantageous in wearable systems and devices that use dry electrodes to employ circuitry that mitigates the effect of such noise phenomenon (e.g., by detecting when high impedances at electrode-skin interfaces may cause measured signals to be of low quality).

The present disclosure is generally directed to passively measuring the impedances of electrode/skin interfaces using the contributions of intrinsic current noise on the outputs of biopotential signal amplifiers (e.g., using any suitable time-domain and/or frequency-domain analysis method). The power spectral densities of amplifier output signals may include one or more frequency ranges that are expected to contain mostly biopotential signals (e.g., EMG signals) and one or more frequency ranges that are expected to contain mostly noise. Measured noise power of the latter frequency ranges may be dominated by current noise power, especially when interface impedances at electrode-skin interfaces are high. As will be explained in greater detail below, the systems and methods described herein may measure the noise power in these noise-dominated frequency ranges in order to infer or estimate interface impedances. The impedances of electrode/skin interfaces may be continually monitored for contact/on-arm detection, channel quality diagnosis, and/or user feedback (e.g., users can be instructed to adjust wearable devices to reduce high interface impedances when appropriate). By monitoring channel quality, signals of low-quality channels may be ignored and/or their contributions lessened in downstream signal processing.

Features from any of the embodiments described herein may be used in combination with one another in accordance with the general principles described herein. These and other embodiments, features, and advantages will be more fully understood upon reading the following detailed description in conjunction with the accompanying drawings and claims.

Figure 6:
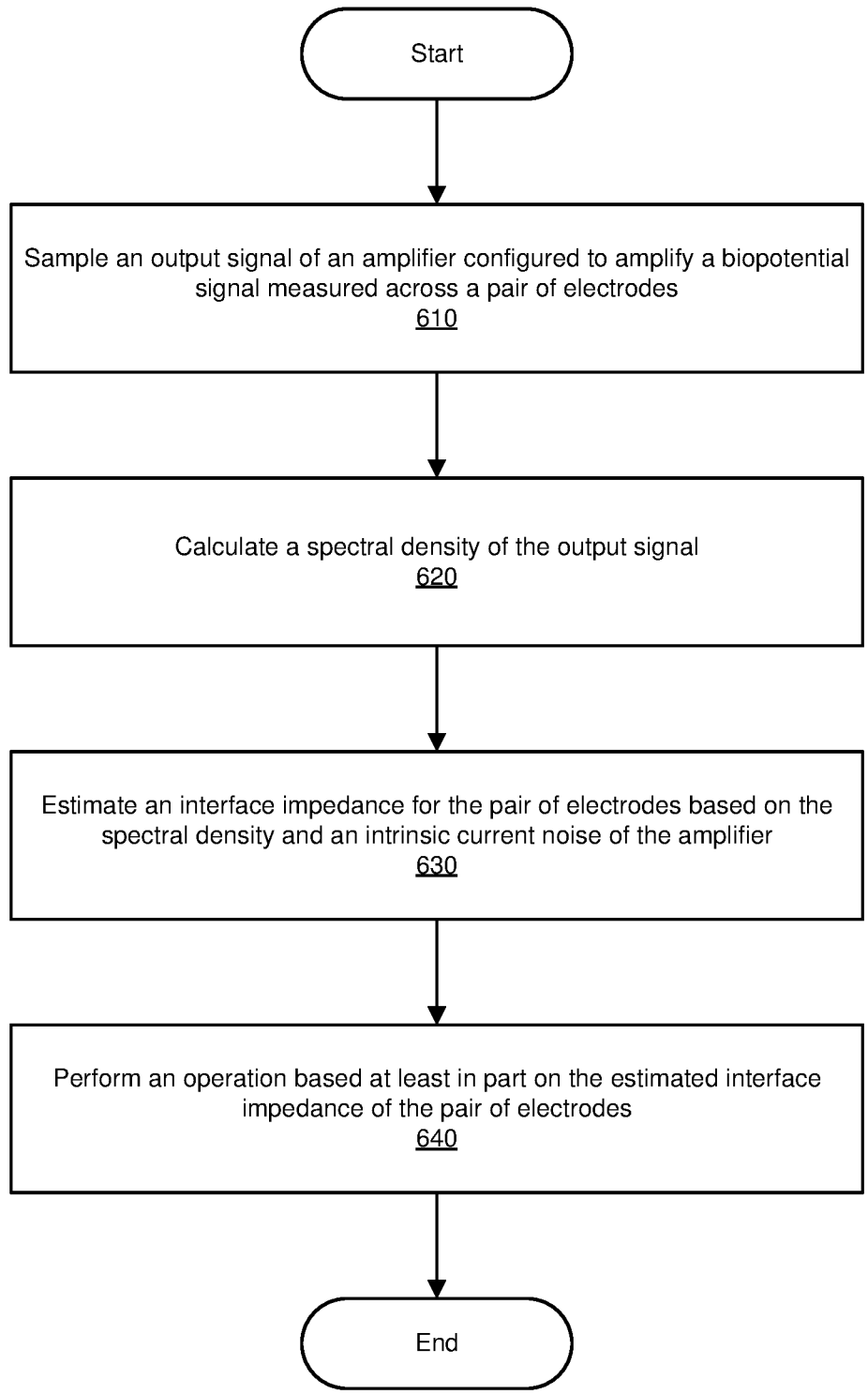
FIG. 6 is a flow diagram of an exemplary method for utilizing intrinsic current noise to measure interface impedance, according to some embodiments.
Figure 7:
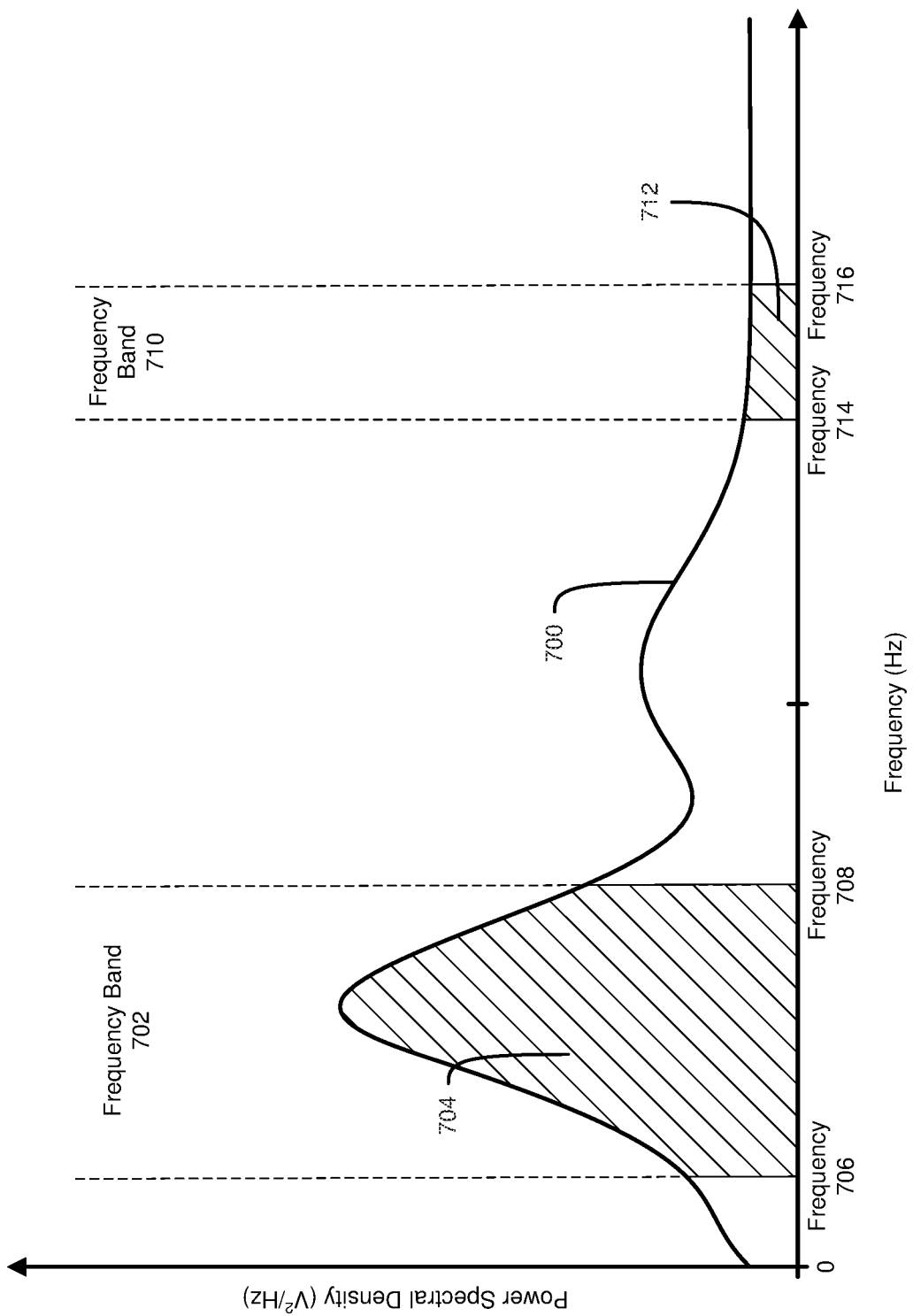
FIG. 7 is a graph illustrating an exemplary power spectral density curve corresponding to an exemplary amplifier output signal, in accordance with some embodiments.

The following will provide, with reference to FIGS. 1-5, detailed descriptions of exemplary biosignal sensing systems. The descriptions corresponding to FIGS. 6 and 7 provide detailed descriptions of exemplary methods for utilizing intrinsic current noise to measure interface impedances. Finally, with reference to FIGS. 8-16, the following will provide detailed descriptions of various extended-reality systems and components that may implement embodiments of the present disclosure.

Figure 2:
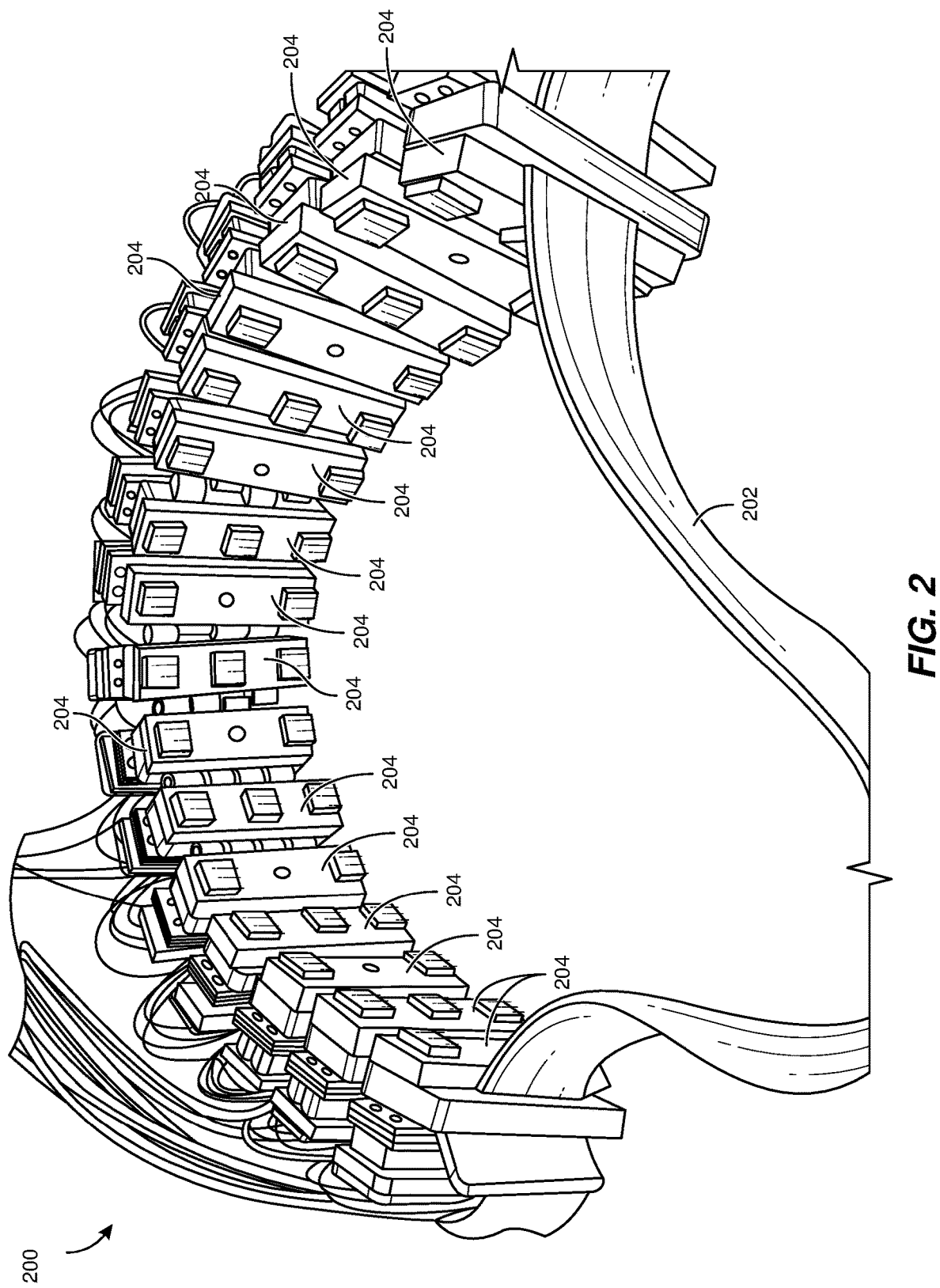
FIG. 2 illustrates a wearable device having neuromuscular activity sensors arranged circumferentially thereon, in accordance with some embodiments.

FIG. 1 schematically illustrates components of a biosignal sensing system 100 in accordance with some embodiments. System 100 includes a pair of electrodes 110 (e.g., a pair of dry surface electrodes) configured to register or measure a biosignal (e.g., an Electrooculography (EOG) signal, an Electromyography (EMG) signal, a surface Electromyography (sEMG) signal, an Electroencephalography (EEG) signal, an Electrocardiography (ECG) signal, etc.) generated by the body of a user 102 (e.g., for electrophysiological monitoring or stimulation). In some embodiments, both of electrodes 110 may be contact electrodes configured to contact a user's skin. In other embodiments, both of electrodes 110 may be non-contact electrodes configured to not contact a user's skin. Alternatively, one of electrodes 110 may be a contact electrode configured to contact a user's skin, and the other one of electrodes 110 may be a non-contact electrode configured to not contact the user's skin. In some embodiments, electrodes 110 may be arranged as a portion of a wearable device configured to be worn on or around part of a user's body. For example, in one nonlimiting example, a plurality of electrodes including electrodes 110 may be arranged circumferentially around an adjustable and/or elastic band such as a wristband or armband configured to be worn around a user's wrist or arm (e.g., as illustrated in FIG. 2). Additionally or alternatively, at least some of electrodes 110 may be arranged on a wearable patch configured to be affixed to or placed in contact with a portion of the body of user 102. In some embodiments, the electrodes may be minimally invasive and may include one or more conductive components placed in or through all or part of the skin or dermis of the user. It should be appreciated that any suitable number of electrodes may be used, and the number and arrangement of electrodes may depend on the particular application for which a device is used.

Biosignals (e.g., biopotential signals) measured or recorded by electrodes 110 may be small, and amplification of the biosignals recorded by electrodes 110 may be desired. As shown in FIG. 1, electrodes 110 may be coupled to amplification circuitry 111 configured to amplify the biosignals conducted by electrodes 110. Amplification circuitry 111 may include any suitable amplifier. Examples of suitable amplifiers may include operational amplifiers, differential amplifiers that amplify differences between two input voltages, instrumental amplifiers (e.g., differential amplifiers having input buffer amplifiers), single ended amplifiers, and/or any other suitable amplifier capable of amplifying biosignals.

As shown in FIG. 1, an output of amplification circuitry 111 may be provided to analog-to-digital converter (ADC) circuitry 114, which may convert amplified biosignals to digital signals for further processing by a microprocessor 116. In some embodiments, microprocessor 116 may process the digital signals to measure or estimate the interface impedances of one or more of electrodes 110, as will be explained in greater detail below. Microprocessor 116 may be implemented by one or more hardware processors. In some embodiments, electrodes 110, amplification circuitry 111, ADC circuitry 114, and/or microprocessor 116 may represent some or all of a biosignal sensor. The processed signals output from microprocessor 116 may be interpreted by a host machine 120, examples of which include, but are not limited to, a desktop computer, a laptop computer, a smartwatch, a smartphone, a head-mounted display device, or any other computing device. In some implementations, host machine 120 may be configured to output one or more control signals for controlling a physical or virtual device based, at least in part, on an analysis of the signals output from microprocessor 116. As shown, biosignal sensing system 100 may include additional sensors 118, which may be configured to record types of information about a state of a user other than biosignal information. For example, sensors 118 may include, temperature sensors configured to measure skin/electrode temperature, inertial measurement unit (IMU) sensors configured to measure movement information such as rotation and acceleration, humidity sensors, and other bio-chemical sensors configured to provide information about the user and/or the user's environment.

In one implementation, sixteen neuromuscular activity sensors including electrodes 110 may be arranged circumferentially around an elastic band configured to be worn around a user's lower arm. For example, FIG. 2 shows sEMG sensors 204 arranged circumferentially around elastic band 202. It should be appreciated that any suitable number of neuromuscular activity sensors having any suitable number of electrodes (including wet and/or dry electrodes) may be used and the number and arrangement of sensors/electrodes may depend on the particular application for which the wearable device is used. For example, as shown in FIG. 2, some of the sEMG sensors 204 include two sEMG electrodes, whereas others of the sEMG sensors 204 include three sEMG electrodes, with the middle of the three electrodes being a ground electrode. The ground electrode may be included on one or more of the sEMG sensors 204 to, for example, further bias the skin potential and/or to filter out noise. Although the schematic diagrams in FIGS. 1 and 3-5, illustrates only two electrodes being connected to an amplifier/amplification circuitry, it should be appreciated that for sEMG sensors 204 in which three (or more) electrodes are used, a corresponding number of connections between the electrodes and the amplifier/amplification circuitry would be included.

Figure 3:
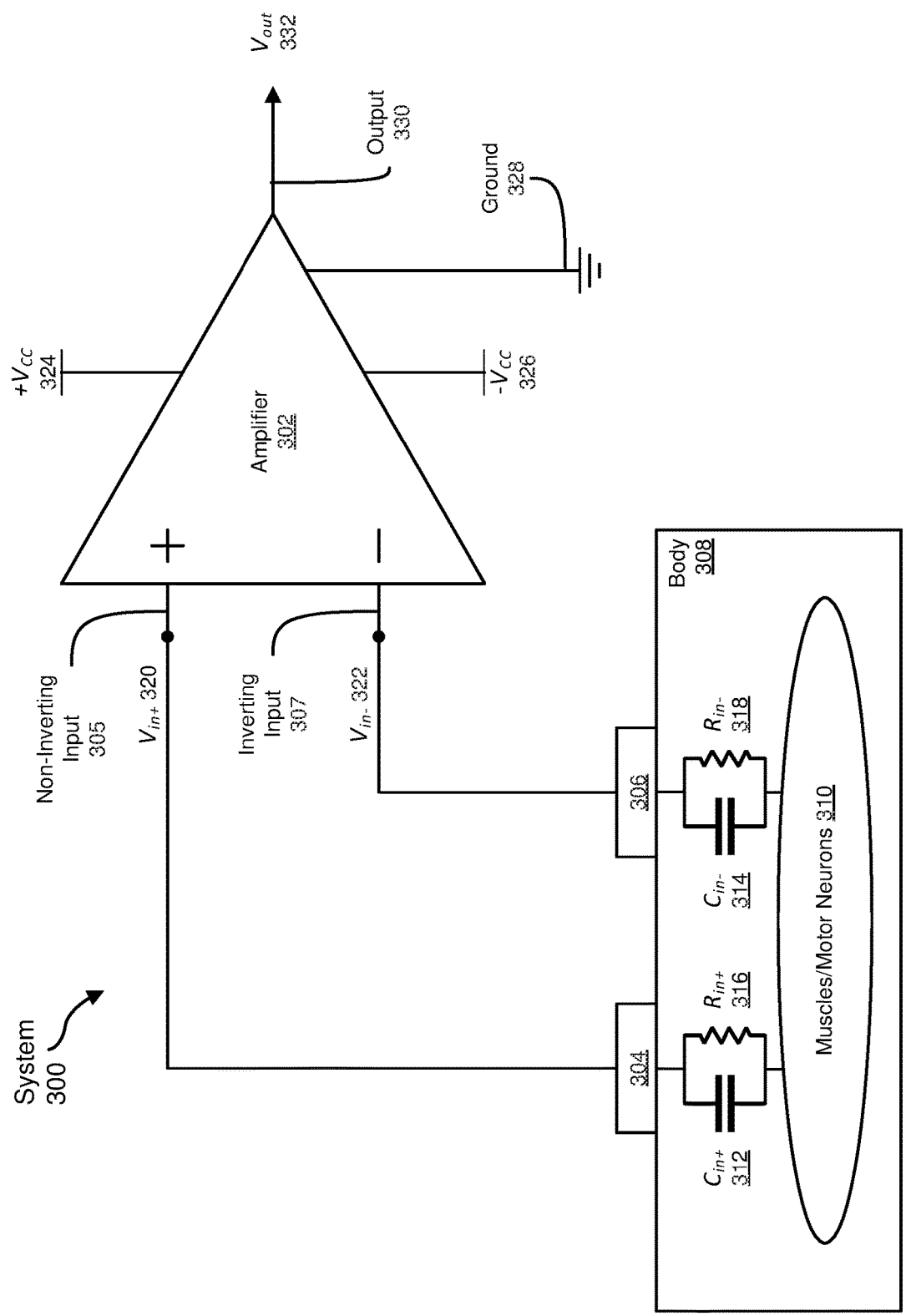
FIG. 3 is a circuit diagram of an exemplary system for amplifying a voltage difference between two electrodes, in accordance with some embodiments.

One illustrative implementation of amplification circuitry 111 shown in FIG. 1 is illustrated in FIG. 3, according to some embodiments. In the example of system 300 shown in FIG. 3, a differential amplifier 302 (e.g., an instrumentation amplifier) may be electrically coupled to a user's body 308, having muscles and motor neurons 310, via electrodes 304 and 306 (which are, for example, instances of electrodes 110 shown in FIG. 1, and which may include any combination of wet and/or dry sEMG electrodes). The methods described herein may be implemented with any suitable amplifier (e.g., amplifiers with either single-ended input or differential inputs). Here an amplifier with differential inputs is used as an example. In this example, electrode 304 and electrode 306 are electrically coupled to a non-inverting input 305 and an inverting input 307 of amplifier 302, respectively. Due to the nature of contact afforded by electrodes 304 and 306, the coupling between each of electrodes 304 and 306 and body 308 may have associated capacitances 312 ($C_{in+}$) and 314 ($C_{in-}$), respectively. Additionally or alternatively, the coupling between each of electrodes 304 and 306 and body 310 may have associated resistances 316 ($R_{in+}$) and 318 ($R_{in-}$), respectively. The values of these resistances and capacitances may vary due to, for example, one or more of variation in skin conditions (e.g., hydration levels, amounts of intervening body hair), differing amounts of physical contact between the respective electrode and skin, and/or manufacturing variations between electrodes 304 and 306.

In the example of FIG. 3, biosignals (e.g., from muscles and/or motor neurons 310) conducted by electrodes 304 and 306 may be provided to inputs 305 and 307 of amplifier 302, as input voltages 320 ($v_{in+}$) and 322 ($v_{in-}$), respectively. In this example, amplifier 302 may be powered using a dual power supply with voltage 324 (+$v_{cc}$) as a positive supply and voltage 326 (-$v_{cc}$) as a negative supply with respect to a ground 328. An amplified signal produced by amplifier 302 may be produced at output 330 as output voltage 332 ($v_{out}$) according to equation (1), wherein G is the gain of amplifier 302. While not illustrated in FIG. 3, body 308 may be coupled to ground 328 via one or more additional electrodes.

$$v_{out}=G*(v_{in+}-v_{in-}) \quad (1)$$

For an ideal amplifier in ideal conditions, a measured difference between inputs 305 and 307 (e.g., $v_{in+}-v_{in-}$) may contain only a biopotential signal of interest. However, the inputs/outputs of real-world amplifiers are generally affected by various intrinsic and extrinsic noise sources. One source of noise in biopotential sensing systems is intrinsic voltage noise. As used herein, intrinsic voltage noise may refer to voltage noise created by the circuitry that receives and/or processes raw biopotential signals. Intrinsic voltage noise may include voltage noise arising from receiving circuitry (e.g., amplification, digitizing, and/or signal processing circuitry, etc.), rather than noise introduced into the signals by an external source. Intrinsic voltage noise may be measured, for example, by creating a short circuit between the inputs of the circuitry (or, in a single-ended system, by connecting the single-ended input(s) to ground) such that no signals appear at the inputs to the circuitry, and by measuring the voltage at the output(s) of the circuitry.

Another source of noise in biopotential sensing systems is interface voltage noise (e.g., noise generated by current noise in contact with a user's skin). As used herein, interface voltage noise may refer to voltage noise that is introduced into a system when electrodes are placed in contact with a user's body (e.g., the user's skin). Interface voltage noise may be measured, for example, by applying electrodes (e.g., to the user's skin), measuring the voltage at the output(s) of the circuitry that receives the signals, and subtracting the known intrinsic voltage noise. In some instances, interface voltage noise may arise from electrode-skin interfaces due to intrinsic current noise present or detected in the receiving circuitry. For instance, intrinsic current noise may combine with an impedance at the electrode-skin interface to create interface voltage noise. The resulting interface voltage noise may be high due to high impedance at the electrode-skin interface, which may be affected by the condition of the skin (e.g., density of hair, etc.), the contact area of the electrode, and other such considerations. When interface impedances are low, output signals may be dominated by intrinsic voltage noise. When interface impedances are high, output signals may be dominated by intrinsic current noise. In at least one embodiment, the disclosed systems may implement amplifiers with proportionally higher intrinsic current noise so that the noise power of the amplifier's output signals will be dominated by current noise power.

Figure 4:
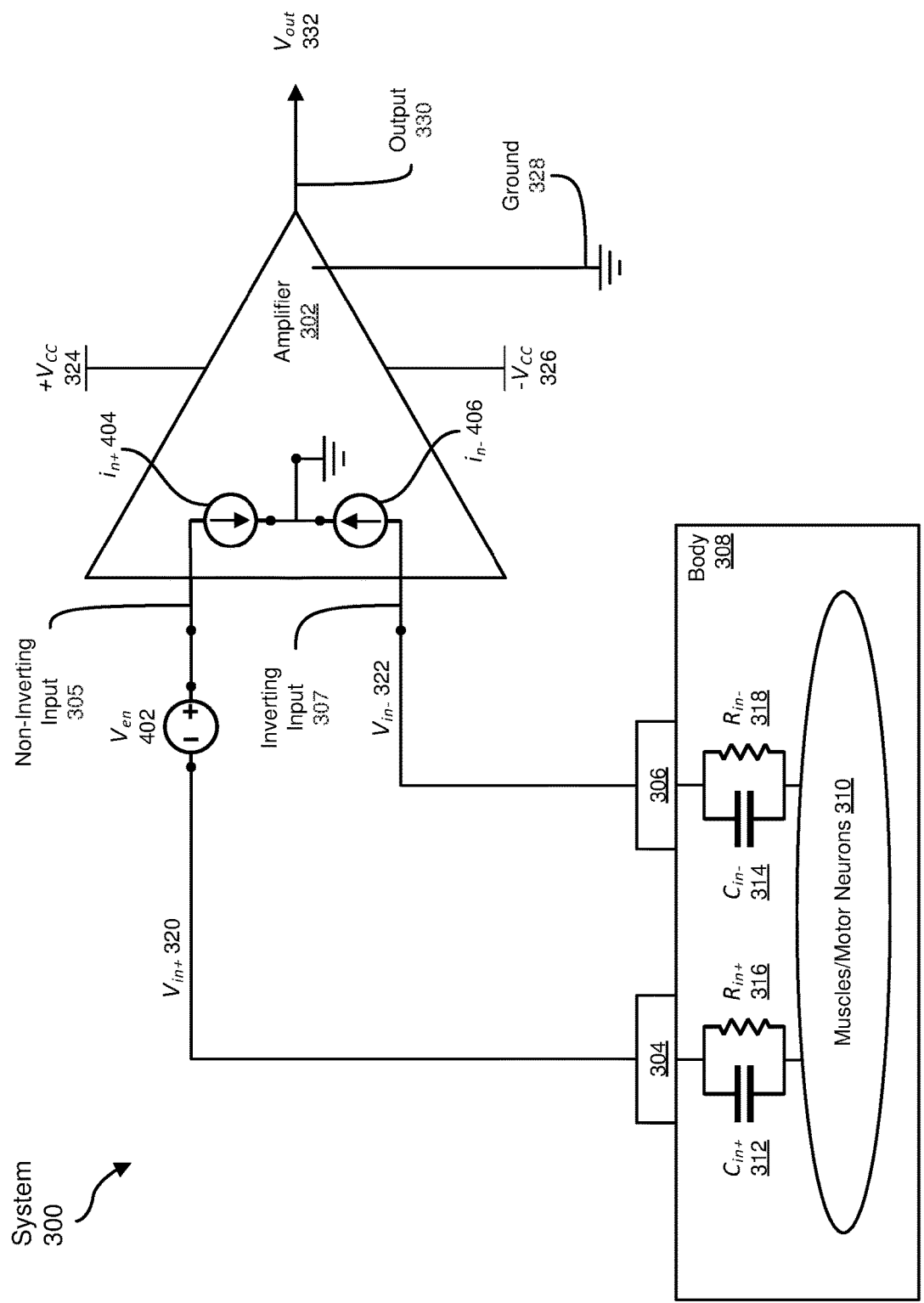
FIG. 4 is a circuit diagram showing a model of the intrinsic noise sources of the exemplary system of FIG. 3, in accordance with some embodiments.

FIG. 4 illustrates a noise model wherein amplifier 302 includes an intrinsic voltage noise ($v_{en}$) and intrinsic current noises 404 ($i_{n+}$) and 406 ($i_{n-}$). Intrinsic voltage noise 402 is illustrated here as a voltage source 402 at the positive terminal of amplifier 302 that would have an equivalent contribution to output voltage 332. Current noise 404 is illustrated as a current source into (or out of) the positive terminal of amplifier 302, and current noise 406 is illustrated as a current source into (or out of) the negative terminal of amplifier 302. Current noise may interact with the interface resistances of electrodes 304 and 306 such that the current noise contributions to output voltage 332 may be written as $i_{n+} \times R_{in+}$ at the positive terminal and $i_{n-} \times R_{in-}$ at the negative terminal. In some examples, current noises 404 and 406 may be equal and independent sources on each input such that $i_{n-}=i_{n+}$.

Figure 5:
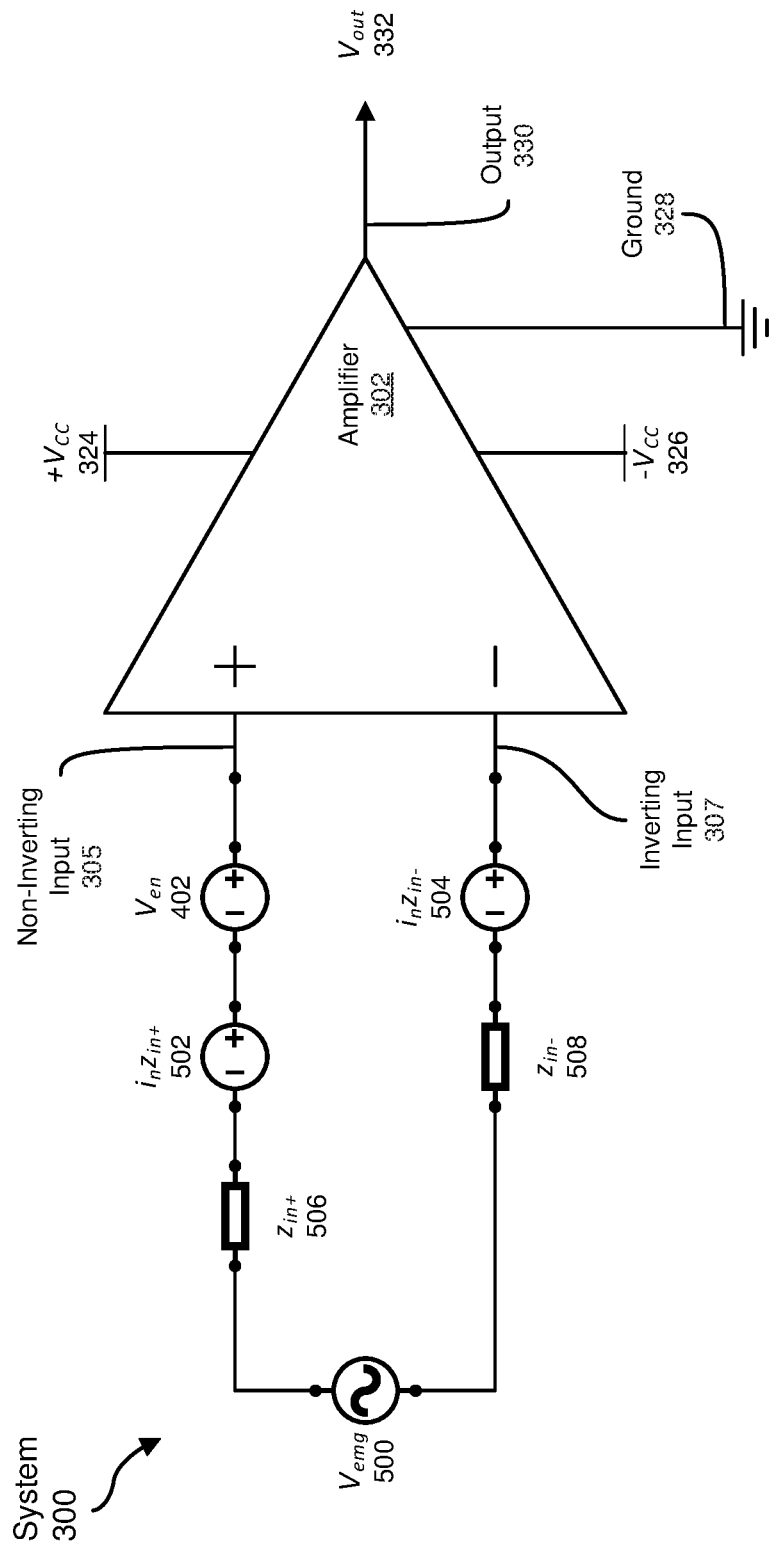
FIG. 5 is a circuit diagram showing a simplified model of the intrinsic noise sources of the exemplary system of FIG. 3, in accordance with some embodiments.

FIG. 5 illustrates a simplified noise model of the intrinsic noise sources of amplifier 302 configured to amplify a sEMG signal 500 ($v_{emg}$). In this simplified noise model, the contribution of intrinsic current noises 404 and 406 to output voltage 332 are shown as voltage sources 502 ($i_n z_{in+}$) and 504 ($i_n z_{in-}$) in series with corresponding interface impedances 506 ($z_{in+}$) and 508 ($z_{in-}$). In this example, output voltage 332 may be expressed by equation (2) and/or equation (3). As can be seen, higher values for interface impedances 506 and/or 508 may result in higher contributions of current noises 404 and 406 to output voltage 332, while lower values for interface impedances 506 and/or 508 may result in lower contributions of current noises 404 and 406 to output voltage 332.

$$v_{out}=G*(v_{emg}+i_n z_{in+}+i_n z_{in-}+v_{en}) \quad (2)$$

$$v_{out}=G*(v_{emg}+i_n(z_{in+}+z_{in-})+v_{en}) \quad (3)$$

FIG. 6 is a flow diagram of an exemplary computer-implemented method 600 for utilizing intrinsic current noise to measure interface impedances. The steps shown in FIG. 6 may be performed by any suitable computing circuitry, computer-executable code, and/or computing system, including the components(s) illustrated in FIG. 1. In one example, each of the steps shown in FIG. 6 may represent an algorithm whose structure includes and/or is represented by multiple sub-steps, examples of which will be provided in greater detail below.

As illustrated in FIG. 6, at step 610 one or more of the systems described herein may sample an output signal of an amplifier configured to amplify a biopotential signal measured across a pair of electrodes. For example, microprocessor 116 in FIG. 1 may sample output voltage 332 of amplifier 302 as shown in FIG. 3. The disclosed systems may sample the output signal of an amplifier at any sampling rate and/or for any time period suitable for the particular application for which a wearable device is being used. In one embodiment, the disclosed systems may sample the output signal of an sEMG amplifier at a sampling rate of at least 1 kHz for at least 1 second. In other embodiments, the disclosed systems may sample the output signal of an sEMG amplifier at a sampling rate of at least 2 kHz.

In some embodiments, an amplifier may be capable of sensing signals from any combination of two electrodes found in an array of electrodes. In such embodiments, the described systems may sample the output signal of the amplifier when coupled to two or more of the possible combinations. In at least one embodiment, the systems disclosed herein may infer a single electrode's interface impedance by analyzing the interface impedances, determined in the manner disclosed below, of each pair of electrodes to which the single electrode has belonged.

At step 620, one or more of the systems described herein may calculate a spectral density (e.g., a power spectral density) of the output signal. For example, microprocessor 116 may calculate power spectral density 700 in FIG. 7 for output voltage 332 of amplifier 302 in FIG. 3. In some examples, the term "spectral density" may refer to any representation of the distribution of power for the frequency components of an input signal and/or any equivalent time domain based representation or operation from which the distribution of power for the frequency components of an input signal may be estimated or determined. The term "spectral density" may refer to a power spectral density, a voltage spectral density, or a current spectral density. In some embodiments, the disclosed systems may perform a Fourier transform (or any other suitable type of time-frequency transformation) on a time-domain signal to generate a representation of the signal in the frequency domain. For example, the systems described herein may calculate a spectral density of an output signal using a suitable frequency-domain analysis method such as a Fast Fourier Transform (FFT) or a Short-Time Fourier Transform (STFT).

FIG. 7 illustrates an exemplary Power Spectral Density (PSD) curve 700 of an exemplary amplifier's output signal. In this example, a frequency band 702 may represent a frequency band that is expected to include most or all of the frequency components of a biopotential signal of interest (e.g., a sEMG signal). As such, area 704 under curve 700 within frequency band 702 may represent the power present in the biopotential signal. As shown in FIG. 7, frequency band 702 may be defined by a lower frequency 706 and an upper frequency 708. In some examples, lower frequency 706 may have a value withing the range of 50 Hz to 150 Hz, and upper frequency 708 may have a value within the range of 500 Hz to 800 Hz. In another example, lower frequency 706 may have a value withing the range of 50 Hz to 150 Hz, and upper frequency 708 may have a value within the range of 300 Hz to 500 Hz. In at least one example, lower frequency 706 may have a value of approximately 100 Hz, and upper frequency 708 may have a value of approximately 500 Hz.

A frequency band 710 of PSD curve 700 may represent a frequency band that is not expected to include much or any of the frequency components of a biopotential signal of interest and/or a frequency band containing mostly noise power. As such, area 712 under curve 700 within frequency band 710 may represent a portion of the noise power in an amplifier's output signal. As shown in FIG. 7, frequency band 710 may be defined by a lower frequency 714 and an upper frequency 716. In some examples, lower frequency 714 may have a value withing the range of 500 Hz to 900 Hz, and upper frequency 716 may have a value within the range of 700 Hz to 1100 Hz. In at least one example, lower frequency 714 may have a value of approximately 700 Hz, and upper frequency 716 may have a value of approximately 900 Hz. In some examples, lower frequency 714 may have a value greater than 1100 Hz.

At step 630, one or more of the systems described herein may estimate an interface impedance for the two electrodes based on the spectral density and a predetermined intrinsic current noise of the amplifier. For example, microprocessor 116 may estimate an interface impedance for electrodes 304 and/or 306 based on spectral density 700 and a predetermined intrinsic current noise of amplifier 302.

The disclosed systems may estimate an interface impedance based on a spectral density of an amplifier's output signal in a variety of ways. In one example, the disclosed systems may compare a calculated spectral density with a database of spectral-density profiles of the same type of amplifier in order to estimate an interface impedance for the amplifier. In some examples, amplifiers of the same type (e.g., amplifiers with the same or similar intrinsic current noise) may generate similar spectral densities when their interface impedances are similar. For at least this reason, a mapping may be predetermined (e.g., in the lab using test samples) that associates spectral density profiles with interface impedances that have been measured through other means (e.g., applying a known voltage across a pair of electrodes and measuring the current that passes through the interface between the electrodes and a user's skin). Such a mapping may be used to indirectly estimate interface impedances in real time based on a spectral density of an amplifier output signal without any direct measurement of the interface impedance or the hardware necessary for such direct measurements.

In other examples, the disclosed systems may use a power spectral density of an amplifier's output signal to estimate an interface impedance by (1) calculating a noise power of the output signal over a predetermined frequency band (e.g., by integrating the power spectral density over the predetermined frequency band) and (2) estimating the interface impedance based on the noise power. The disclosed systems may calculate a noise power over a frequency band that is not expected to include much or any of the frequency components of a biopotential signal of interest, a frequency band containing mostly noise power, and/or a frequency band containing mostly current noise power. In some examples, the noise power (e.g., expressed with units of Vrms) within a particular frequency range may be equal to or proportional to the interface impedance of an amplifier multiplied by the amplifier's current noise (e.g., as shown by equation (4)). As such, the disclosed systems may estimate the amplifier's interface impedance by solving for ($z_{in+}$+ $z_{in-}$) in equation (5), where $F_{upper}$ and $F_{lower}$ are the upper and lower frequencies of the frequency range, respectively.

$$\text{Noise Power} \propto (z_{in+} + z_{in-}) * i_n \quad (4)$$

$$(z_{in+} + z_{in-}) = \frac{\text{Noise Power}/\sqrt{(F_{upper} - F_{lower})}}{i_n} \quad (5)$$

In some examples, the disclosed systems may compare an amplifier's calculated noise power with a database of noise powers previously calculated for the same type of amplifier in order to estimate an interface impedance for the amplifier. In some examples, amplifiers of the same type (e.g., amplifiers with the same or similar intrinsic current noise) may have similar noise powers within certain frequency bands when their interface impedances are similar. For at least this reason, a mapping may be predetermined (e.g., in the lab using test samples) that associates noise powers and/or frequency bands with interface impedances that have been measured through other means (e.g., applying a known voltage across a pair of electrodes and measuring the current that passes through the interface between the electrodes and a user's skin). Such a mapping may be used to indirectly estimate interface impedances based on real-time noise power calculations without any direct measurement of the interface impedances or the hardware necessary for such direct measurements.

At step 640, one or more of the systems described herein may perform an operation based at least in part on the estimated interface impedance. The disclosed systems may perform some or all of the operations disclosed herein based on estimated interface impedances. In some examples, the disclosed systems may perform an operation based on whether an estimated interface impedance is above or below a predetermined threshold value, based on whether an estimated interface impedance falls outside of an expected or desired range, based on whether an estimated interface impedance remains stable over time, and/or whether an estimated interface impedance suddenly changes or spikes. For example, the disclosed system may determine that one or more of a wearable device's electrodes are not in contact or in poor contact with a user's body or the wearable device is not being worn by the user if an interface impedance associated with one or more pairs of its electrodes is estimated to be sufficiently high.

In some examples, the disclosed systems may, in response to a high interface impedance, ask the user to put on or adjust the wearable device until the interface impedance of the pair of electrodes has improved. In another example, the disclosed systems may, in response to a high interface impedance, place the wearable device in an energy saving mode (e.g., by deactivating the signal channel associated with the high interface impedance). Additionally or alternatively, the disclosed systems may, in response to a high interface impedance, reconfigure how the electrodes of the wearable device are paired and/or how the signals measured via certain pairs of electrodes are processed. In some examples, an amplifier's output signal may be weighted in downstream processing based on the interface impedances of its electrodes. As such, downstream processes may be performed using the highest quality input signals. As mentioned above, the disclosed systems may continuously or periodically monitor the impedances of electrode/skin interfaces for contact/on-arm detection, channel quality diagnosis, and/or user feedback. By monitoring channel quality, the disclosed systems may ignore signals of low-quality channels and/or may lessen their contributions in downstream signal processing operations.

EXAMPLE EMBODIMENTS

Example 1: A computer-implemented method may include (1) sampling an output signal of an amplifier that amplifies a voltage difference between two electrodes, (2) calculating, based on a power spectral density of the output signal, a noise power of the output signal over a predetermined frequency band, (3) estimating an interface impedance of at least one of the two electrodes based on the noise power and a predetermined intrinsic current noise of the amplifier, (4) and performing an operation based at least in part on the estimated interface impedance.

Example 2: The computer-implemented method of Example 1, wherein (1) the output signal of the amplifier may include (a) a first component corresponding to a biopotential signal obtained from a user's body via the two electrodes, (b) a second component corresponding to an intrinsic voltage noise of the amplifier, and (c) a third component corresponding to a voltage resulting from the intrinsic current noise of the amplifier across and the electrode-skin interfaces between the two electrodes and the user's body and (2) the third component contributes more to the noise power of the output signal over the predetermined frequency band that either of the first component and the second component.

Example 3: The computer-implemented method of Example 1 or 2, wherein performing the operation may include (1) determining, based on the estimated interface impedance being above a predetermined threshold, that one of the two electrodes is not in contact with a user's body and (2) performing an energy-saving operation in response to the one of the two electrodes not being in contact with the user's body.

Example 4: The computer-implemented method of any of Examples 1-3, wherein performing the operation may include (1) determining, based on the estimated interface impedance being above a predetermined threshold, that one of the two electrodes is in poor contact with a user's body and (2) instructing the user to adjust a positioning of the one of the two electrodes relative to the user's body.

Example 5: The computer-implemented method of any of Examples 1-4, wherein performing the operation may include (1) determining, based on the estimated interface impedance being above a predetermined threshold, that a quality of the output signal is low and (2) refraining from using the output signal to perform a downstream operation in response to the quality of the output signal being low.

Example 6: The computer-implemented method of any of Examples 1-5, wherein performing the operation may include (1) determining, based on the estimated interface impedance dropping below a predetermined threshold, that a quality of the output signal is high and (2) using the output signal to perform a downstream operation in response to the quality of the output signal being high.

Example 7: The computer-implemented method of any of Examples 1-6, wherein the output signal of the amplifier may include a neuromuscular signal from a user's body, and performing the operation may include estimating a gesture of the user based on the neuromuscular signal and the estimated interface impedance.

Example 8: The computer-implemented method of any of Examples 1-7, wherein calculating the noise power may include integrating the power spectral density over the predetermined frequency band.

Example 9: The computer-implemented method of any of Examples 1-8, wherein estimating the interface impedance may include dividing the noise power by the frequency band and the predetermined intrinsic current noise of the amplifier.

Example 10: The computer-implemented method of any of Examples 1-9, wherein the predetermined frequency band may be within 700 Hz to 900 Hz.

Example 11: The computer-implemented method of any of Examples 1-10, wherein the predetermined frequency band may be above 1 kHz.

Example 12: The computer-implemented method of any of Examples 1-11, wherein the amplifier is a physiological amplifier operable to amplify one or more of surface electromyography signals, electrocardiography signals, electroencephalography signals, sonomyography signals, or electrical impedance tomography signals.

Example 13: A wearable device for detecting neuromuscular activity, may include (1) at least two dry electrodes configured to electrically couple to a body surface of a wearer of the wearable device, (2) signal-amplifying circuitry configured to amplify electrical signals from the at least two dry electrodes, and (3) impedance-measuring circuitry that estimates an interface impedance of at least one of the two dry electrodes based on a spectral density of an output signal of the signal-amplifying circuitry and a predetermined intrinsic current noise of the signal-amplifying circuitry, and performing an operation based at least in part on the estimated interface impedance.

Example 14: The wearable device of Example 13, wherein the electrically coupling may include physical contact between the at least two dry electrodes and the body surface of the wearer.

Example 15: The wearable device of Example 13 or 14, wherein the electrically coupling may include capacitive coupling between the at least two dry electrodes and the body surface of the wearer.

Example 16: The wearable device of any of Examples 13-15, wherein (1) the impedance-measuring circuitry may estimate the interface impedance by (1) calculating a power spectral density of the output signal, (2) calculating, using the power spectral density, a noise power of the output signal over a predetermined frequency band, and (3) the impedance-measuring circuitry may estimate the interface impedance based on the noise power.

Example 17: The wearable device of any of Examples 13-16, wherein the signal-amplifying circuitry may include a differential amplifier.

Example 18: The wearable device of any of Examples 13-17 wherein the at least two dry electrodes comprise a pair of dry electrodes and the electrical signals comprise differential signals received by the pair of dry electrodes.

Example 19: The wearable device of any of Examples 13-18, wherein the at least two dry electrodes further comprise a dry ground electrode configured to receive ground signals from which the differential signals are referenced.

Example 20: A wearable arm or wrist band system may include (1) a surface electromyography sensor that detects surface electromyography signals from a user and (2) at least one physical processor that calculates a power spectral density of an output signal of the surface electromyography sensor, calculates, using the power spectral density, a noise power of the output signal over a predetermined frequency band, estimates an interface impedance of the surface electromyography sensor based on the noise power and a predetermined intrinsic current noise of the surface electromyography sensor, and performs an operation based at least in part on the estimated interface impedance.

Embodiments of the present disclosure may include or be implemented in conjunction with various types of artificial-reality systems. Artificial reality is a form of reality that has been adjusted in some manner before presentation to a user, which may include, for example, a virtual reality, an augmented reality, a mixed reality, a hybrid reality, or some combination and/or derivative thereof. Artificial-reality content may include completely computer-generated content or computer-generated content combined with captured (e.g., real-world) content. The artificial-reality content may include video, audio, haptic feedback, or some combination thereof, any of which may be presented in a single channel or in multiple channels (such as stereo video that produces a three-dimensional (3D) effect to the viewer). Additionally, in some embodiments, artificial reality may also be associated with applications, products, accessories, services, or some combination thereof, that are used to, for example, create content in an artificial reality and/or are otherwise used in (e.g., to perform activities in) an artificial reality.

Artificial-reality systems may be implemented in a variety of different form factors and configurations. Some artificial-reality systems may be designed to work without near-eye displays (NEDs). Other artificial-reality systems may include an NED that also provides visibility into the real world (such as, e.g., augmented-reality system 800 in FIG. 8) or that visually immerses a user in an artificial reality (such as, e.g., virtual-reality system 900 in FIG. 9). While some artificial-reality devices may be self-contained systems, other artificial-reality devices may communicate and/or coordinate with external devices to provide an artificial-reality experience to a user. Examples of such external devices include handheld controllers, mobile devices, desktop computers, devices worn by a user, devices worn by one or more other users, and/or any other suitable external system.

Figure 8:
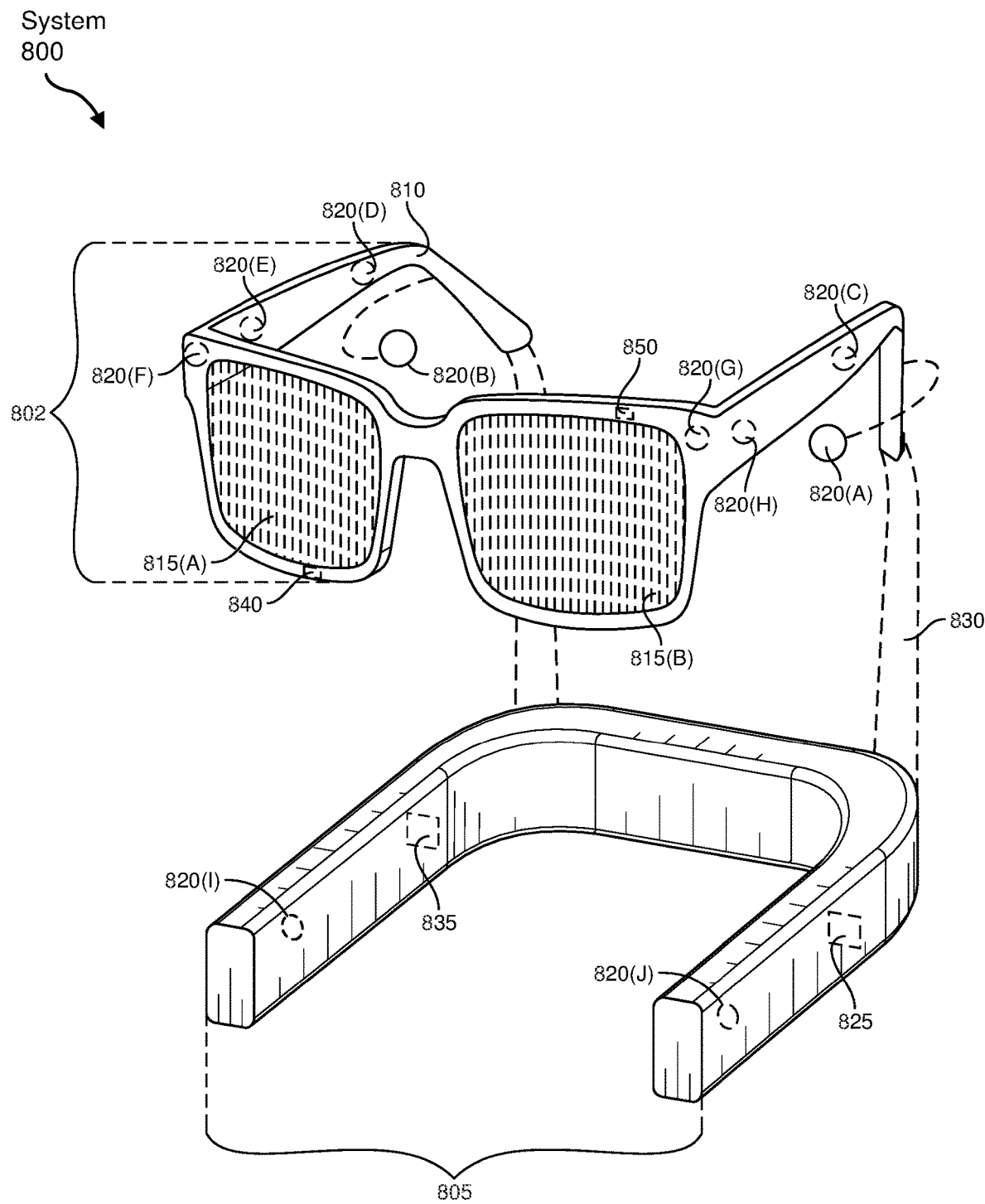
FIG. 8 is an illustration of exemplary augmented-reality glasses that may be used in connection with embodiments of this disclosure.

Turning to FIG. 8, augmented-reality system 800 may include an eyewear device 802 with a frame 810 configured to hold a left display device 815(A) and a right display device 815(B) in front of a user's eyes. Display devices 815(A) and 815(B) may act together or independently to present an image or series of images to a user. While augmented-reality system 800 includes two displays, embodiments of this disclosure may be implemented in augmented-reality systems with a single NED or more than two NEDs.

In some embodiments, augmented-reality system 800 may include one or more sensors, such as sensor 840. Sensor 840 may generate measurement signals in response to motion of augmented-reality system 800 and may be located on substantially any portion of frame 810. Sensor 840 may represent one or more of a variety of different sensing mechanisms, such as a position sensor, an inertial measurement unit (IMU), a depth camera assembly, a structured light emitter and/or detector, or any combination thereof. In some embodiments, augmented-reality system 800 may or may not include sensor 840 or may include more than one sensor. In embodiments in which sensor 840 includes an IMU, the IMU may generate calibration data based on measurement signals from sensor 840. Examples of sensor 840 may include, without limitation, accelerometers, gyroscopes, magnetometers, other suitable types of sensors that detect motion, sensors used for error correction of the IMU, or some combination thereof.

In some examples, augmented-reality system 800 may also include a microphone array with a plurality of acoustic transducers 820(A)-820(J), referred to collectively as acoustic transducers 820. Acoustic transducers 820 may represent transducers that detect air pressure variations induced by sound waves. Each acoustic transducer 820 may be configured to detect sound and convert the detected sound into an electronic format (e.g., an analog or digital format). The microphone array in FIG. 8 may include, for example, ten acoustic transducers: 820(A) and 820(B), which may be designed to be placed inside a corresponding ear of the user, acoustic transducers 820(C), 820(D), 820(E), 820(F), 820(G), and 820(H), which may be positioned at various locations on frame 810, and/or acoustic transducers 820(1) and 820(J), which may be positioned on a corresponding neckband 805.

In some embodiments, one or more of acoustic transducers 820(A)-(J) may be used as output transducers (e.g., speakers). For example, acoustic transducers 820(A) and/or 820(B) may be earbuds or any other suitable type of headphone or speaker.

The configuration of acoustic transducers 820 of the microphone array may vary. While augmented-reality system 800 is shown in FIG. 8 as having ten acoustic transducers 820, the number of acoustic transducers 820 may be greater or less than ten. In some embodiments, using higher numbers of acoustic transducers 820 may increase the amount of audio information collected and/or the sensitivity and accuracy of the audio information. In contrast, using a lower number of acoustic transducers 820 may decrease the computing power required by an associated controller 850 to process the collected audio information. In addition, the position of each acoustic transducer 820 of the microphone array may vary. For example, the position of an acoustic transducer 820 may include a defined position on the user, a defined coordinate on frame 810, an orientation associated with each acoustic transducer 820, or some combination thereof.

Acoustic transducers 820(A) and 820(B) may be positioned on different parts of the user's ear, such as behind the pinna, behind the tragus, and/or within the auricle or fossa. Or, there may be additional acoustic transducers 820 on or surrounding the ear in addition to acoustic transducers 820 inside the ear canal. Having an acoustic transducer 820 positioned next to an ear canal of a user may enable the microphone array to collect information on how sounds arrive at the ear canal. By positioning at least two of acoustic transducers 820 on either side of a user's head (e.g., as binaural microphones), augmented-reality device 800 may simulate binaural hearing and capture a 3D stereo sound field around about a user's head. In some embodiments, acoustic transducers 820(A) and 820(B) may be connected to augmented-reality system 800 via a wired connection 830, and in other embodiments acoustic transducers 820(A) and 820(B) may be connected to augmented-reality system 800 via a wireless connection (e.g., a BLUETOOTH connection). In still other embodiments, acoustic transducers 820(A) and 820(B) may not be used at all in conjunction with augmented-reality system 800.

Acoustic transducers 820 on frame 810 may be positioned in a variety of different ways, including along the length of the temples, across the bridge, above or below display devices 815(A) and 815(B), or some combination thereof. Acoustic transducers 820 may also be oriented such that the microphone array is able to detect sounds in a wide range of directions surrounding the user wearing the augmented-reality system 800. In some embodiments, an optimization process may be performed during manufacturing of augmented-reality system 800 to determine relative positioning of each acoustic transducer 820 in the microphone array.

In some examples, augmented-reality system 800 may include or be connected to an external device (e.g., a paired device), such as neckband 805. Neckband 805 generally represents any type or form of paired device. Thus, the following discussion of neckband 805 may also apply to various other paired devices, such as charging cases, smart watches, smart phones, wrist bands, other wearable devices, hand-held controllers, tablet computers, laptop computers, other external compute devices, etc.

As shown, neckband 805 may be coupled to eyewear device 802 via one or more connectors. The connectors may be wired or wireless and may include electrical and/or non-electrical (e.g., structural) components. In some cases, eyewear device 802 and neckband 805 may operate independently without any wired or wireless connection between them. While FIG. 8 illustrates the components of eyewear device 802 and neckband 805 in example locations on eyewear device 802 and neckband 805, the components may be located elsewhere and/or distributed differently on eyewear device 802 and/or neckband 805. In some embodiments, the components of eyewear device 802 and neckband 805 may be located on one or more additional peripheral devices paired with eyewear device 802, neckband 805, or some combination thereof.

Pairing external devices, such as neckband 805, with augmented-reality eyewear devices may enable the eyewear devices to achieve the form factor of a pair of glasses while still providing sufficient battery and computation power for expanded capabilities. Some or all of the battery power, computational resources, and/or additional features of augmented-reality system 800 may be provided by a paired device or shared between a paired device and an eyewear device, thus reducing the weight, heat profile, and form factor of the eyewear device overall while still retaining desired functionality. For example, neckband 805 may allow components that would otherwise be included on an eyewear device to be included in neckband 805 since users may tolerate a heavier weight load on their shoulders than they would tolerate on their heads. Neckband 805 may also have a larger surface area over which to diffuse and disperse heat to the ambient environment. Thus, neckband 805 may allow for greater battery and computation capacity than might otherwise have been possible on a stand-alone eyewear device. Since weight carried in neckband 805 may be less invasive to a user than weight carried in eyewear device 802, a user may tolerate wearing a lighter eyewear device and carrying or wearing the paired device for greater lengths of time than a user would tolerate wearing a heavy standalone eyewear device, thereby enabling users to more fully incorporate artificial-reality environments into their day-to-day activities.

Neckband 805 may be communicatively coupled with eyewear device 802 and/or to other devices. These other devices may provide certain functions (e.g., tracking, localizing, depth mapping, processing, storage, etc.) to augmented-reality system 800. In the embodiment of FIG. 8, neckband 805 may include two acoustic transducers (e.g., 820(1) and 820(J)) that are part of the microphone array (or potentially form their own microphone subarray). Neckband 805 may also include a controller 825 and a power source 835.

Acoustic transducers 820(1) and 820(J) of neckband 805 may be configured to detect sound and convert the detected sound into an electronic format (analog or digital). In the embodiment of FIG. 8, acoustic transducers 820(1) and 820(J) may be positioned on neckband 805, thereby increasing the distance between the neckband acoustic transducers 820(1) and 820(J) and other acoustic transducers 820 positioned on eyewear device 802. In some cases, increasing the distance between acoustic transducers 820 of the microphone array may improve the accuracy of beamforming performed via the microphone array. For example, if a sound is detected by acoustic transducers 820(C) and 820(D) and the distance between acoustic transducers 820(C) and 820 (D) is greater than, e.g., the distance between acoustic transducers 820(D) and 820(E), the determined source location of the detected sound may be more accurate than if the sound had been detected by acoustic transducers 820(D) and 820(E).

Controller 825 of neckband 805 may process information generated by the sensors on neckband 805 and/or augmented-reality system 800. For example, controller 825 may process information from the microphone array that describes sounds detected by the microphone array. For each detected sound, controller 825 may perform a direction-of-arrival (DOA) estimation to estimate a direction from which the detected sound arrived at the microphone array. As the microphone array detects sounds, controller 825 may populate an audio data set with the information. In embodiments in which augmented-reality system 800 includes an inertial measurement unit, controller 825 may compute all inertial and spatial calculations from the IMU located on eyewear device 802. A connector may convey information between augmented-reality system 800 and neckband 805 and between augmented-reality system 800 and controller 825. The information may be in the form of optical data, electrical data, wireless data, or any other transmittable data form. Moving the processing of information generated by augmented-reality system 800 to neckband 805 may reduce weight and heat in eyewear device 802, making it more comfortable to the user.

Power source 835 in neckband 805 may provide power to eyewear device 802 and/or to neckband 805. Power source 835 may include, without limitation, lithium ion batteries, lithium-polymer batteries, primary lithium batteries, alkaline batteries, or any other form of power storage. In some cases, power source 835 may be a wired power source. Including power source 835 on neckband 805 instead of on eyewear device 802 may help better distribute the weight and heat generated by power source 835.

As noted, some artificial-reality systems may, instead of blending an artificial reality with actual reality, substantially replace one or more of a user's sensory perceptions of the real world with a virtual experience. One example of this type of system is a head-worn display system, such as virtual-reality system 900 in FIG. 9, that mostly or completely covers a user's field of view. Virtual-reality system 900 may include a front rigid body 902 and a band 904 shaped to fit around a user's head. Virtual-reality system 900 may also include output audio transducers 906(A) and 906(B). Furthermore, while not shown in FIG. 9, front rigid body 902 may include one or more electronic elements, including one or more electronic displays, one or more inertial measurement units (IMUS), one or more tracking emitters or detectors, and/or any other suitable device or system for creating an artificial-reality experience.

Artificial-reality systems may include a variety of types of visual feedback mechanisms. For example, display devices in augmented-reality system 800 and/or virtual-reality system 900 may include one or more liquid crystal displays (LCDs), light emitting diode (LED) displays, microLED displays, organic LED (OLED) displays, digital light project (DLP) micro-displays, liquid crystal on silicon (LCoS) micro-displays, and/or any other suitable type of display screen. These artificial-reality systems may include a single display screen for both eyes or may provide a display screen for each eye, which may allow for additional flexibility for varifocal adjustments or for correcting a user's refractive error. Some of these artificial-reality systems may also include optical subsystems having one or more lenses (e.g., conventional concave or convex lenses, Fresnel lenses, adjustable liquid lenses, etc.) through which a user may view a display screen. These optical subsystems may serve a variety of purposes, including to collimate (e.g., make an object appear at a greater distance than its physical distance), to magnify (e.g., make an object appear larger than its actual size), and/or to relay (to, e.g., the viewer's eyes) light. These optical subsystems may be used in a non-pupil-forming architecture (such as a single lens configuration that directly collimates light but results in so-called pincushion distortion) and/or a pupil-forming architecture (such as a multi-lens configuration that produces so-called barrel distortion to nullify pincushion distortion).

In addition to or instead of using display screens, some of the artificial-reality systems described herein may include one or more projection systems. For example, display devices in augmented-reality system 800 and/or virtual-reality system 900 may include micro-LED projectors that project light (using, e.g., a waveguide) into display devices, such as clear combiner lenses that allow ambient light to pass through. The display devices may refract the projected light toward a user's pupil and may enable a user to simultaneously view both artificial-reality content and the real world. The display devices may accomplish this using any of a variety of different optical components, including waveguide components (e.g., holographic, planar, diffractive, polarized, and/or reflective waveguide elements), light-manipulation surfaces and elements (such as diffractive, reflective, and refractive elements and gratings), coupling elements, etc. Artificial-reality systems may also be configured with any other suitable type or form of image projection system, such as retinal projectors used in virtual retina displays.

The artificial-reality systems described herein may also include various types of computer vision components and subsystems. For example, augmented-reality system 800 and/or virtual-reality system 900 may include one or more optical sensors, such as two-dimensional (2D) or 3D cameras, structured light transmitters and detectors, time-of-flight depth sensors, single-beam or sweeping laser rangefinders, 3D LiDAR sensors, and/or any other suitable type or form of optical sensor. An artificial-reality system may process data from one or more of these sensors to identify a location of a user, to map the real world, to provide a user with context about real-world surroundings, and/or to perform a variety of other functions.

The artificial-reality systems described herein may also include one or more input and/or output audio transducers. Output audio transducers may include voice coil speakers, ribbon speakers, electrostatic speakers, piezoelectric speakers, bone conduction transducers, cartilage conduction transducers, tragus-vibration transducers, and/or any other suitable type or form of audio transducer. Similarly, input audio transducers may include condenser microphones, dynamic microphones, ribbon microphones, and/or any other type or form of input transducer. In some embodiments, a single transducer may be used for both audio input and audio output.

In some embodiments, the artificial-reality systems described herein may also include tactile (i.e., haptic) feedback systems, which may be incorporated into headwear, gloves, body suits, handheld controllers, environmental devices (e.g., chairs, floormats, etc.), and/or any other type of device or system. Haptic feedback systems may provide various types of cutaneous feedback, including vibration, force, traction, texture, and/or temperature. Haptic feedback systems may also provide various types of kinesthetic feedback, such as motion and compliance. Haptic feedback may be implemented using motors, piezoelectric actuators, fluidic systems, and/or a variety of other types of feedback mechanisms. Haptic feedback systems may be implemented independent of other artificial-reality devices, within other artificial-reality devices, and/or in conjunction with other artificial-reality devices.

By providing haptic sensations, audible content, and/or visual content, artificial-reality systems may create an entire virtual experience or enhance a user's real-world experience in a variety of contexts and environments. For instance, artificial-reality systems may assist or extend a user's perception, memory, or cognition within a particular environment. Some systems may enhance a user's interactions with other people in the real world or may enable more immersive interactions with other people in a virtual world. Artificial-reality systems may also be used for educational purposes (e.g., for teaching or training in schools, hospitals, government organizations, military organizations, business enterprises, etc.), entertainment purposes (e.g., for playing video games, listening to music, watching video content, etc.), and/or for accessibility purposes (e.g., as hearing aids, visual aids, etc.). The embodiments disclosed herein may enable or enhance a user's artificial-reality experience in one or more of these contexts and environments and/or in other contexts and environments.

As noted, artificial-reality systems 800 and 900 may be used with a variety of other types of devices to provide a more compelling artificial-reality experience. These devices may be haptic interfaces with transducers that provide haptic feedback and/or that collect haptic information about a user's interaction with an environment. The artificial-reality systems disclosed herein may include various types of haptic interfaces that detect or convey various types of haptic information, including tactile feedback (e.g., feedback that a user detects via nerves in the skin, which may also be referred to as cutaneous feedback) and/or kinesthetic feedback (e.g., feedback that a user detects via receptors located in muscles, joints, and/or tendons).

Figure 10:
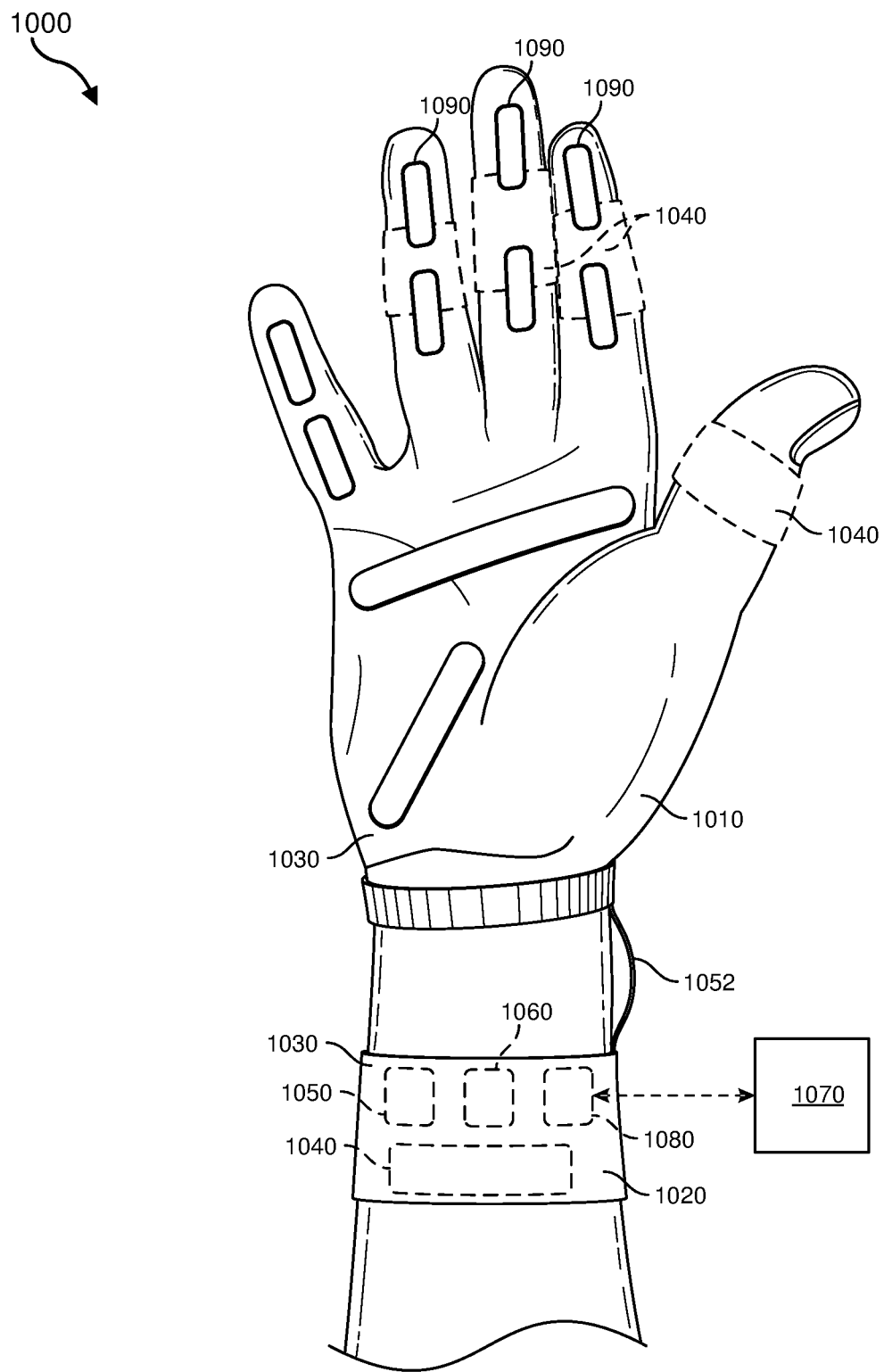
FIG. 10 is an illustration of exemplary haptic devices that may be used in connection with embodiments of this disclosure.

Haptic feedback may be provided by interfaces positioned within a user's environment (e.g., chairs, tables, floors, etc.) and/or interfaces on articles that may be worn or carried by a user (e.g., gloves, wristbands, etc.). As an example, FIG. 10 illustrates a vibrotactile system 1000 in the form of a wearable glove (haptic device 1010) and wristband (haptic device 1020). Haptic device 1010 and haptic device 1020 are shown as examples of wearable devices that include a flexible, wearable textile material 1030 that is shaped and configured for positioning against a user's hand and wrist, respectively. This disclosure also includes vibrotactile systems that may be shaped and configured for positioning against other human body parts, such as a finger, an arm, a head, a torso, a foot, or a leg. By way of example and not limitation, vibrotactile systems according to various embodiments of the present disclosure may also be in the form of a glove, a headband, an armband, a sleeve, a head covering, a sock, a shirt, or pants, among other possibilities. In some examples, the term "textile" may include any flexible, wearable material, including woven fabric, non-woven fabric, leather, cloth, a flexible polymer material, composite materials, etc.

One or more vibrotactile devices 1040 may be positioned at least partially within one or more corresponding pockets formed in textile material 1030 of vibrotactile system 1000. Vibrotactile devices 1040 may be positioned in locations to provide a vibrating sensation (e.g., haptic feedback) to a user of vibrotactile system 1000. For example, vibrotactile devices 1040 may be positioned against the user's finger(s), thumb, or wrist, as shown in FIG. 10. Vibrotactile devices 1040 may, in some examples, be sufficiently flexible to conform to or bend with the user's corresponding body part(s).

A power source 1050 (e.g., a battery) for applying a voltage to the vibrotactile devices 1040 for activation thereof may be electrically coupled to vibrotactile devices 1040, such as via conductive wiring 1052. In some examples, each of vibrotactile devices 1040 may be independently electrically coupled to power source 1050 for individual activation. In some embodiments, a processor 1060 may be operatively coupled to power source 1050 and configured (e.g., programmed) to control activation of vibrotactile devices 1040.

Vibrotactile system 1000 may be implemented in a variety of ways. In some examples, vibrotactile system 1000 may be a standalone system with integral subsystems and components for operation independent of other devices and systems. As another example, vibrotactile system 1000 may be configured for interaction with another device or system 1070. For example, vibrotactile system 1000 may, in some examples, include a communications interface 1080 for receiving and/or sending signals to the other device or system 1070. The other device or system 1070 may be a mobile device, a gaming console, an artificial-reality (e.g., virtual-reality, augmented-reality, mixed-reality) device, a personal computer, a tablet computer, a network device (e.g., a modem, a router, etc.), a handheld controller, etc. Communications interface 1080 may enable communications between vibrotactile system 1000 and the other device or system 1070 via a wireless (e.g., Wi-Fi, BLUETOOTH, cellular, radio, etc.) link or a wired link. If present, communications interface 1080 may be in communication with processor 1060, such as to provide a signal to processor 1060 to activate or deactivate one or more of the vibrotactile devices 1040.

Vibrotactile system 1000 may optionally include other subsystems and components, such as touch-sensitive pads 1090, pressure sensors, motion sensors, position sensors, lighting elements, and/or user interface elements (e.g., an on/off button, a vibration control element, etc.). During use, vibrotactile devices 1040 may be configured to be activated for a variety of different reasons, such as in response to the user's interaction with user interface elements, a signal from the motion or position sensors, a signal from the touch-sensitive pads 1090, a signal from the pressure sensors, a signal from the other device or system 1070, etc.

Although power source 1050, processor 1060, and communications interface 1080 are illustrated in FIG. 10 as being positioned in haptic device 1020, the present disclosure is not so limited. For example, one or more of power source 1050, processor 1060, or communications interface 1080 may be positioned within haptic device 1010 or within another wearable textile.

Figure 11:
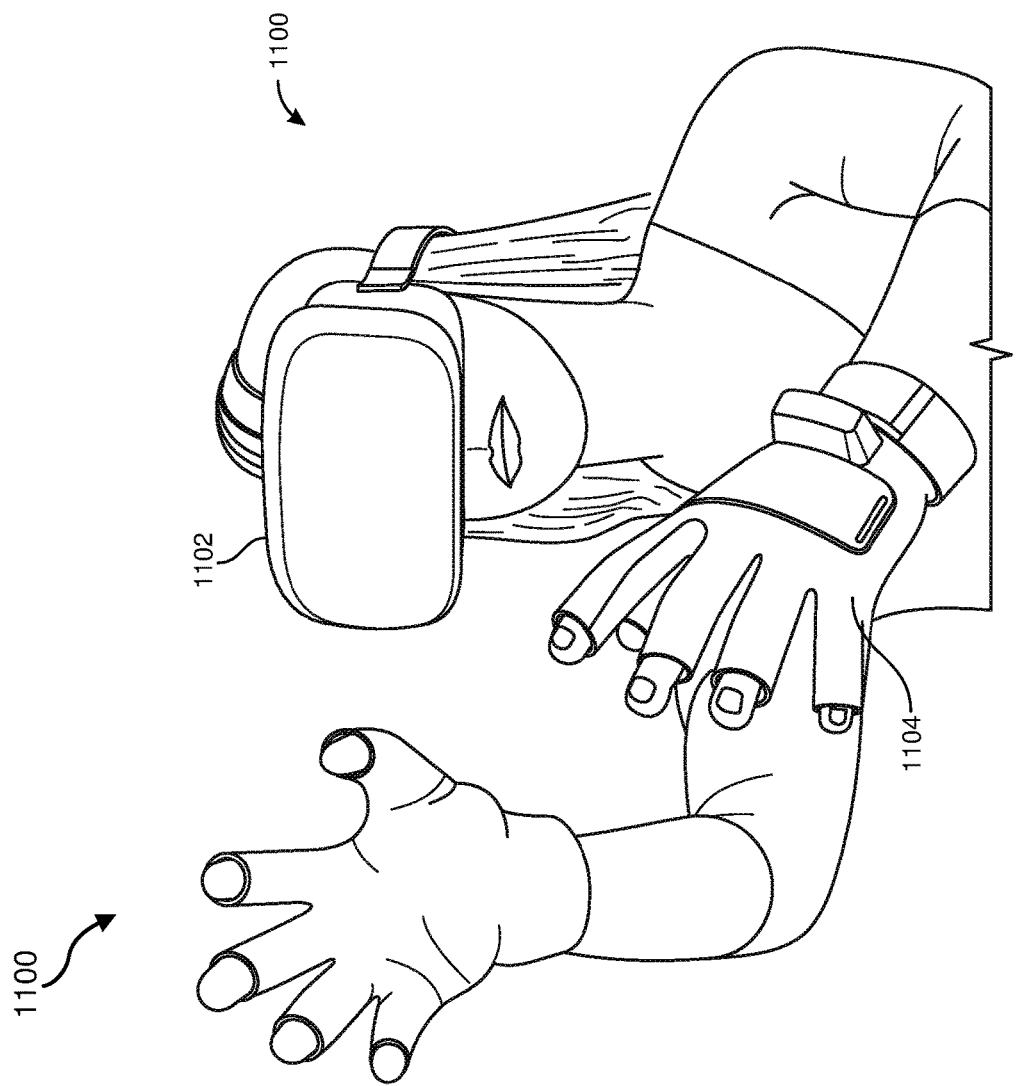
FIG. 11 is an illustration of an exemplary virtual-reality environment according to embodiments of this disclosure.

Haptic wearables, such as those shown in and described in connection with FIG. 10, may be implemented in a variety of types of artificial-reality systems and environments. FIG. 11 shows an example artificial-reality environment 1100 including one head-mounted virtual-reality display and two haptic devices (i.e., gloves), and in other embodiments any number and/or combination of these components and other components may be included in an artificial-reality system. For example, in some embodiments there may be multiple head-mounted displays each having an associated haptic device, with each head-mounted display and each haptic device communicating with the same console, portable computing device, or other computing system.

Figure 9:
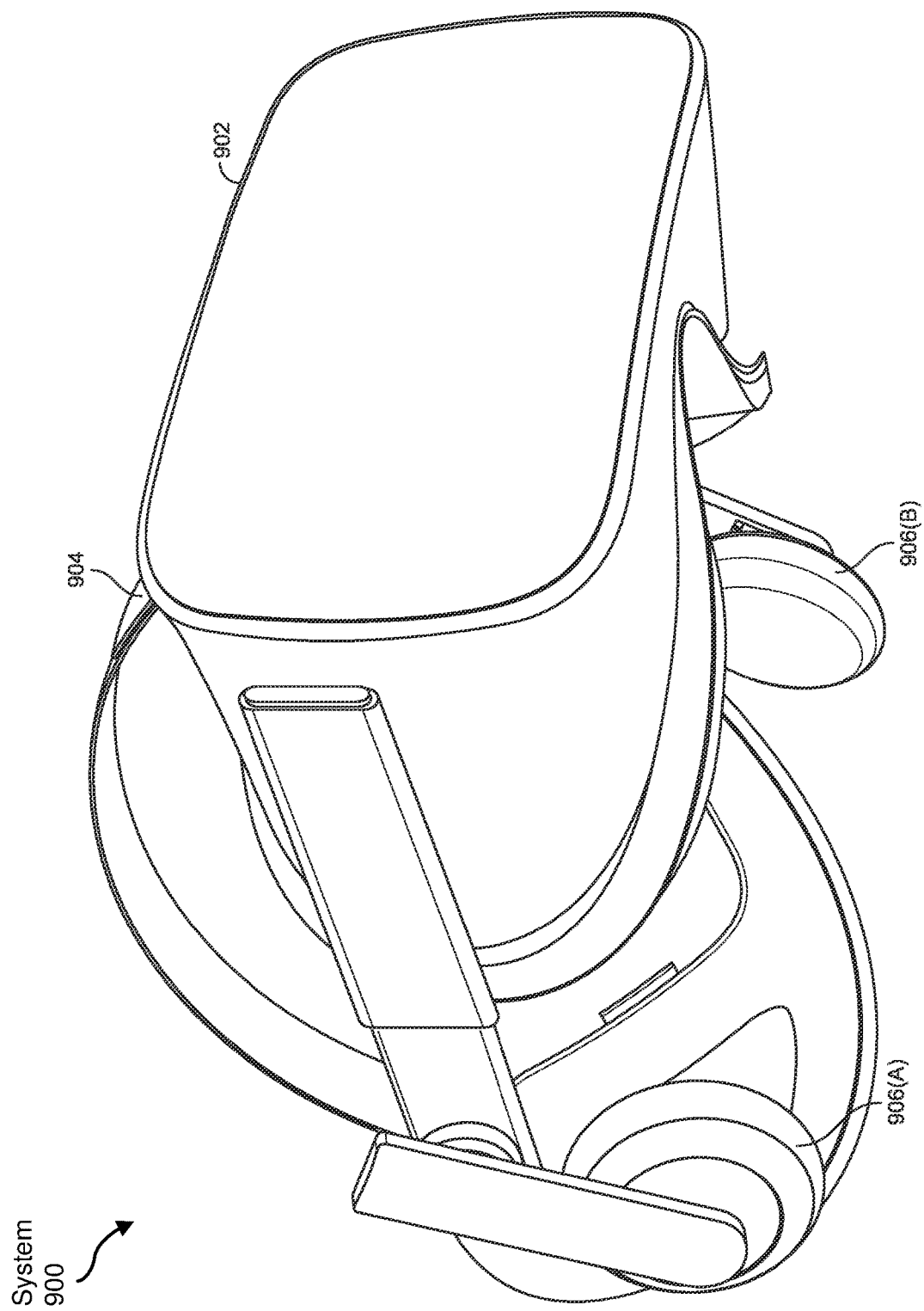
FIG. 9 is an illustration of an exemplary virtual-reality headset that may be used in connection with embodiments of this disclosure.

Head-mounted display 1102 generally represents any type or form of virtual-reality system, such as virtual-reality system 900 in FIG. 9. Haptic device 1104 generally represents any type or form of wearable device, worn by a user of an artificial-reality system, that provides haptic feedback to the user to give the user the perception that he or she is physically engaging with a virtual object. In some embodiments, haptic device 1104 may provide haptic feedback by applying vibration, motion, and/or force to the user. For example, haptic device 1104 may limit or augment a user's movement. To give a specific example, haptic device 1104 may limit a user's hand from moving forward so that the user has the perception that his or her hand has come in physical contact with a virtual wall. In this specific example, one or more actuators within the haptic device may achieve the physical-movement restriction by pumping fluid into an inflatable bladder of the haptic device. In some examples, a user may also use haptic device 1104 to send action requests to a console. Examples of action requests include, without limitation, requests to start an application and/or end the application and/or requests to perform a particular action within the application.

Figure 12:
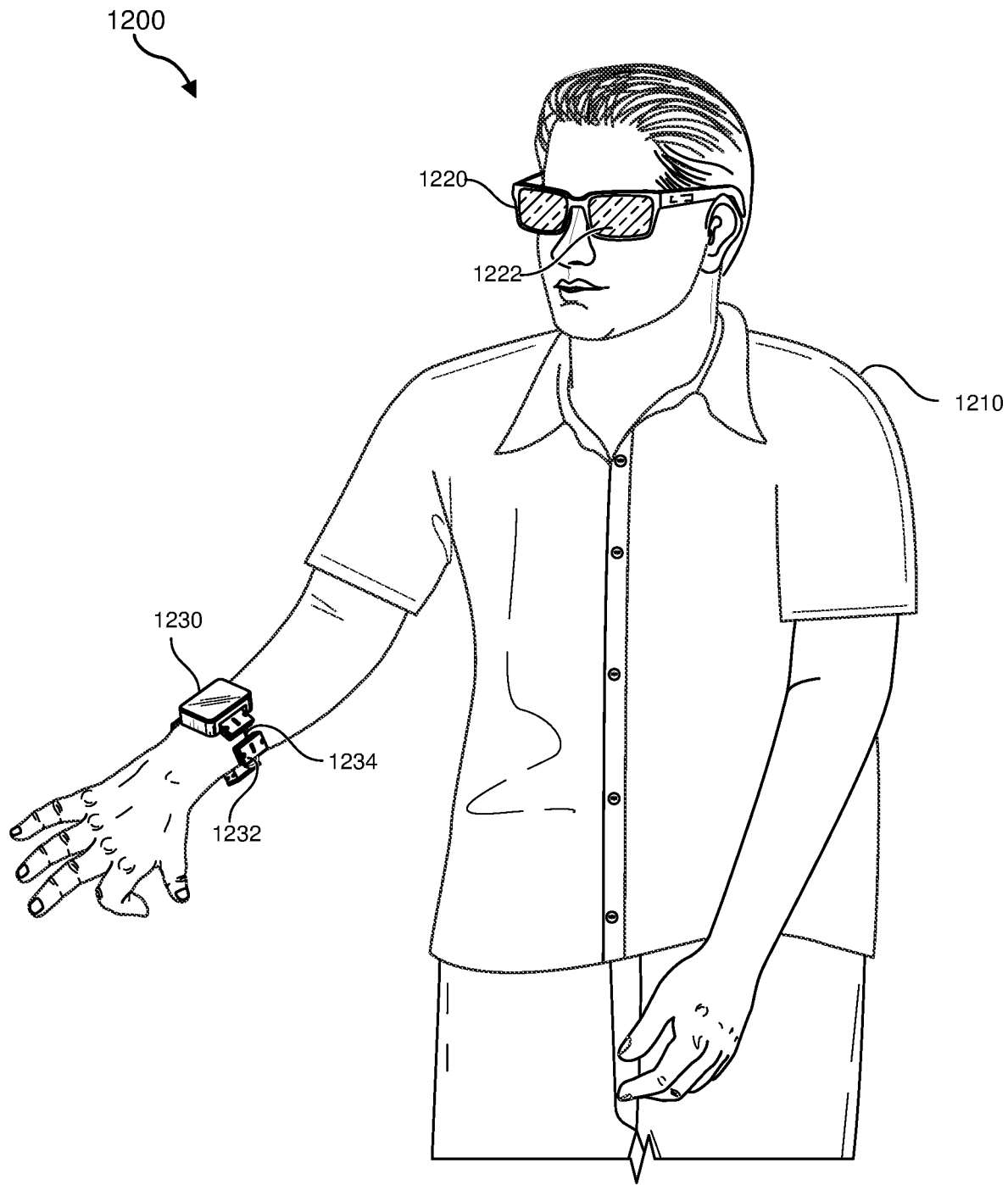
FIG. 12 is an illustration of an exemplary augmented-reality environment according to embodiments of this disclosure.

While haptic interfaces may be used with virtual-reality systems, as shown in FIG. 11, haptic interfaces may also be used with augmented-reality systems, as shown in FIG. 12. FIG. 12 is a perspective view of a user 1210 interacting with an augmented-reality system 1200. In this example, user 1210 may wear a pair of augmented-reality glasses 1220 that may have one or more displays 1222 and that are paired with a haptic device 1230. In this example, haptic device 1230 may be a wristband that includes a plurality of band elements 1232 and a tensioning mechanism 1234 that connects band elements 1232 to one another.

One or more of band elements 1232 may include any type or form of actuator suitable for providing haptic feedback. For example, one or more of band elements 1232 may be configured to provide one or more of various types of cutaneous feedback, including vibration, force, traction, texture, and/or temperature. To provide such feedback, band elements 1232 may include one or more of various types of actuators. In one example, each of band elements 1232 may include a vibrotactor (e.g., a vibrotactile actuator) configured to vibrate in unison or independently to provide one or more of various types of haptic sensations to a user. Alternatively, only a single band element or a subset of band elements may include vibrotactors.

Haptic devices 1010, 1020, 1104, and 1230 may include any suitable number and/or type of haptic transducer, sensor, and/or feedback mechanism. For example, haptic devices 1010, 1020, 1104, and 1230 may include one or more mechanical transducers, piezoelectric transducers, and/or fluidic transducers. Haptic devices 1010, 1020, 1104, and 1230 may also include various combinations of different types and forms of transducers that work together or independently to enhance a user's artificial-reality experience. In one example, each of band elements 1232 of haptic device 1230 may include a vibrotactor (e.g., a vibrotactile actuator) configured to vibrate in unison or independently to provide one or more of various types of haptic sensations to a user.

Figure 13A:
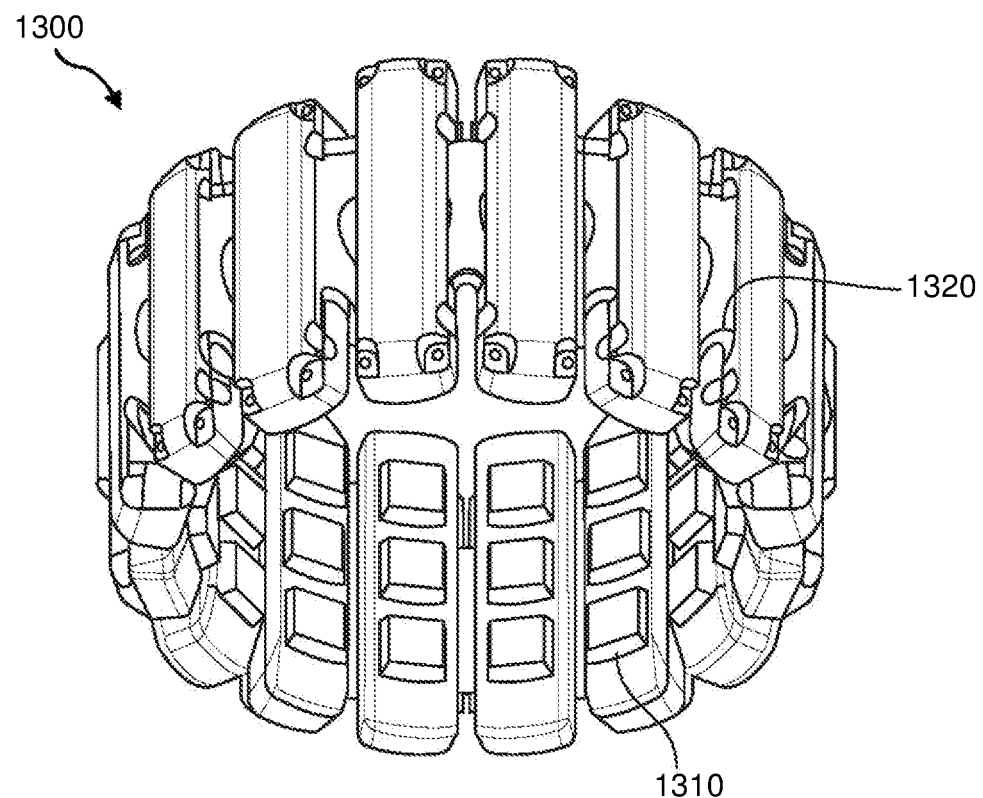
FIGS. 13A and 13B are illustrations of an exemplary human-machine interface configured to be worn around a user's lower arm or wrist.
Figure 13B:
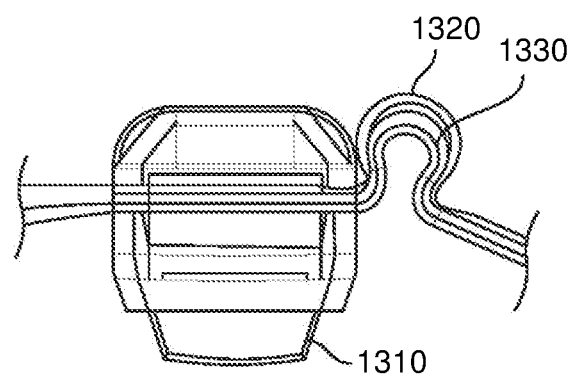

FIG. 13A illustrates an exemplary human-machine interface (also referred to herein as an EMG control interface) configured to be worn around a user's lower arm or wrist as a wearable system 1300. In this example, wearable system 1300 may include sixteen neuromuscular sensors 1310 (e.g., EMG sensors) arranged circumferentially around an elastic band 1320 with an interior surface 930 configured to contact a user's skin. However, any suitable number of neuromuscular sensors may be used. The number and arrangement of neuromuscular sensors may depend on the particular application for which the wearable device is used. For example, a wearable armband or wristband can be used to generate control information for controlling an augmented reality system, a robot, controlling a vehicle, scrolling through text, controlling a virtual avatar, or any other suitable control task. As shown, the sensors may be coupled together using flexible electronics incorporated into the wireless device. FIG. 13B illustrates a cross-sectional view through one of the sensors of the wearable device shown in FIG. 13A. In some embodiments, the output of one or more of the sensing components can be optionally processed using hardware signal processing circuitry (e.g., to perform amplification, filtering, and/or rectification). In other embodiments, at least some signal processing of the output of the sensing components can be performed in software. Thus, signal processing of signals sampled by the sensors can be performed in hardware, software, or by any suitable combination of hardware and software, as aspects of the technology described herein are not limited in this respect. A non-limiting example of a signal processing chain used to process recorded data from sensors 1310 is discussed in more detail below with reference to FIGS. 14A and 14B.

Figure 14A:
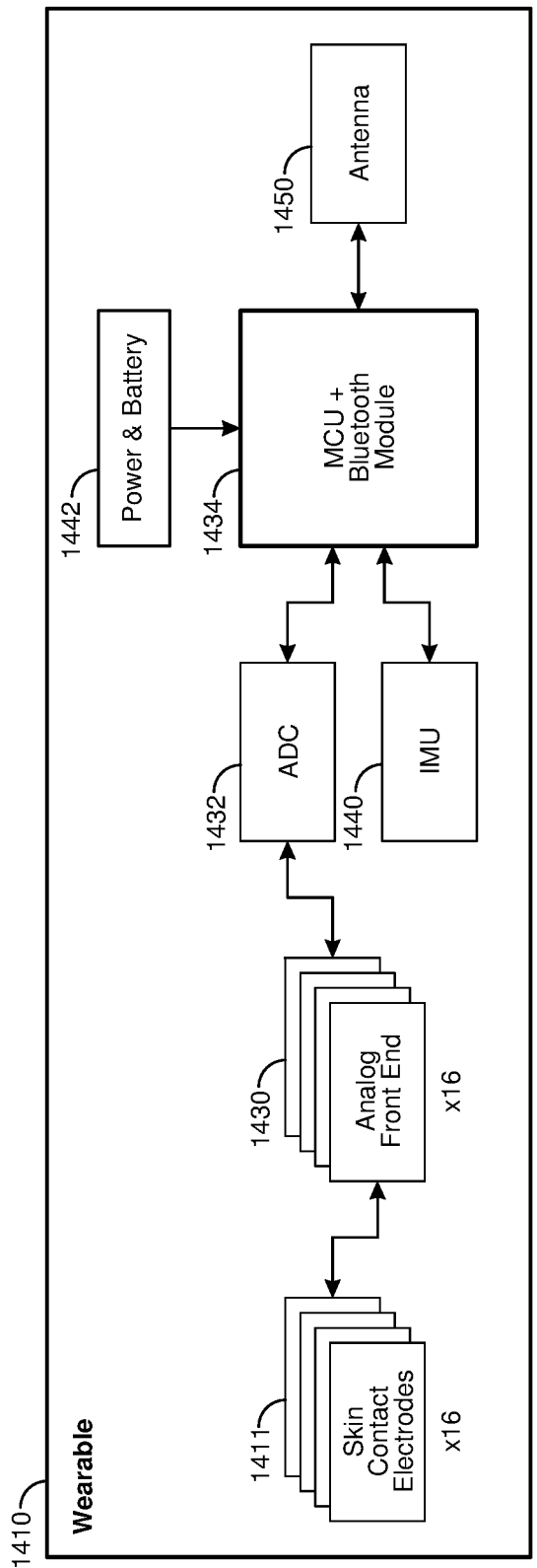
FIGS. 14A and 14B are illustrations of an exemplary schematic diagram with internal components of a wearable system.
Figure 14B:
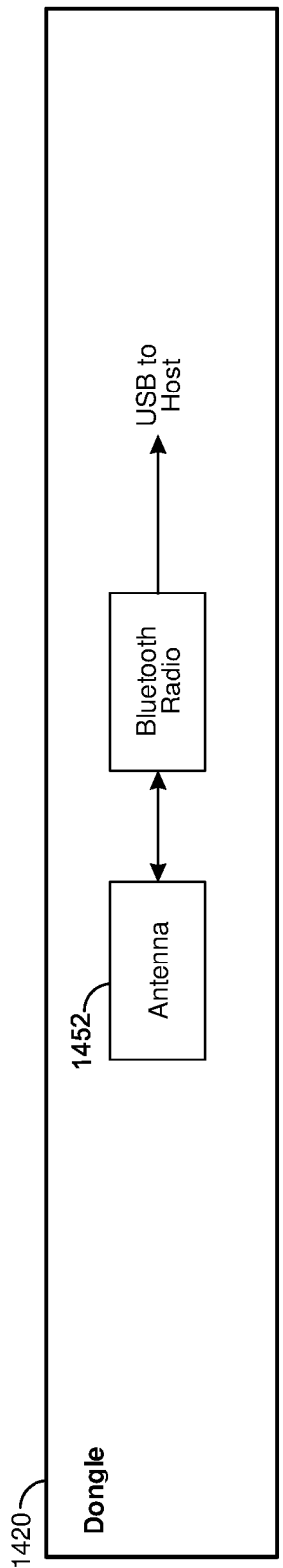

FIGS. 14A and 14B illustrate an exemplary schematic diagram with internal components of a wearable system with EMG sensors. As shown, the wearable system may include a wearable portion 1410 (FIG. 14A) and a dongle portion 1420 (FIG. 14B) in communication with the wearable portion 1410 (e.g., via BLUETOOTH or another suitable wireless communication technology). As shown in FIG. 14A, the wearable portion 1410 may include skin contact electrodes 1411, examples of which are described in connection with FIGS. 13A and 13B. The output of the skin contact electrodes 1411 may be provided to analog front end 1430, which may be configured to perform analog processing (e.g., amplification, noise reduction, filtering, etc.) on the recorded signals. The processed analog signals may then be provided to analog-to-digital converter 1432, which may convert the analog signals to digital signals that can be processed by one or more computer processors. An example of a computer processor that may be used in accordance with some embodiments is microcontroller (MCU) 1434, illustrated in FIG. 14A. As shown, MCU 1434 may also include inputs from other sensors (e.g., IMU sensor 1440), and power and battery module 1442. The output of the processing performed by MCU 1434 may be provided to antenna 1450 for transmission to dongle portion 1420 shown in FIG. 14B.

Dongle portion 1420 may include antenna 1452, which may be configured to communicate with antenna 1450 included as part of wearable portion 1410. Communication between antennas 1450 and 1452 may occur using any suitable wireless technology and protocol, non-limiting examples of which include radiofrequency signaling and BLUETOOTH. As shown, the signals received by antenna 1452 of dongle portion 1420 may be provided to a host computer for further processing, display, and/or for effecting control of a particular physical or virtual object or objects.

Although the examples provided with reference to FIGS. 13A-13B and FIGS. 14A-14B are discussed in the context of interfaces with EMG sensors, the techniques described herein for reducing electromagnetic interference can also be implemented in wearable interfaces with other types of sensors including, but not limited to, mechanomyography (MMG) sensors, sonomyography (SMG) sensors, and electrical impedance tomography (EIT) sensors. The techniques described herein for reducing electromagnetic interference can also be implemented in wearable interfaces that communicate with computer hosts through wires and cables (e.g., USB cables, optical fiber cables, etc.).

Figure 15:
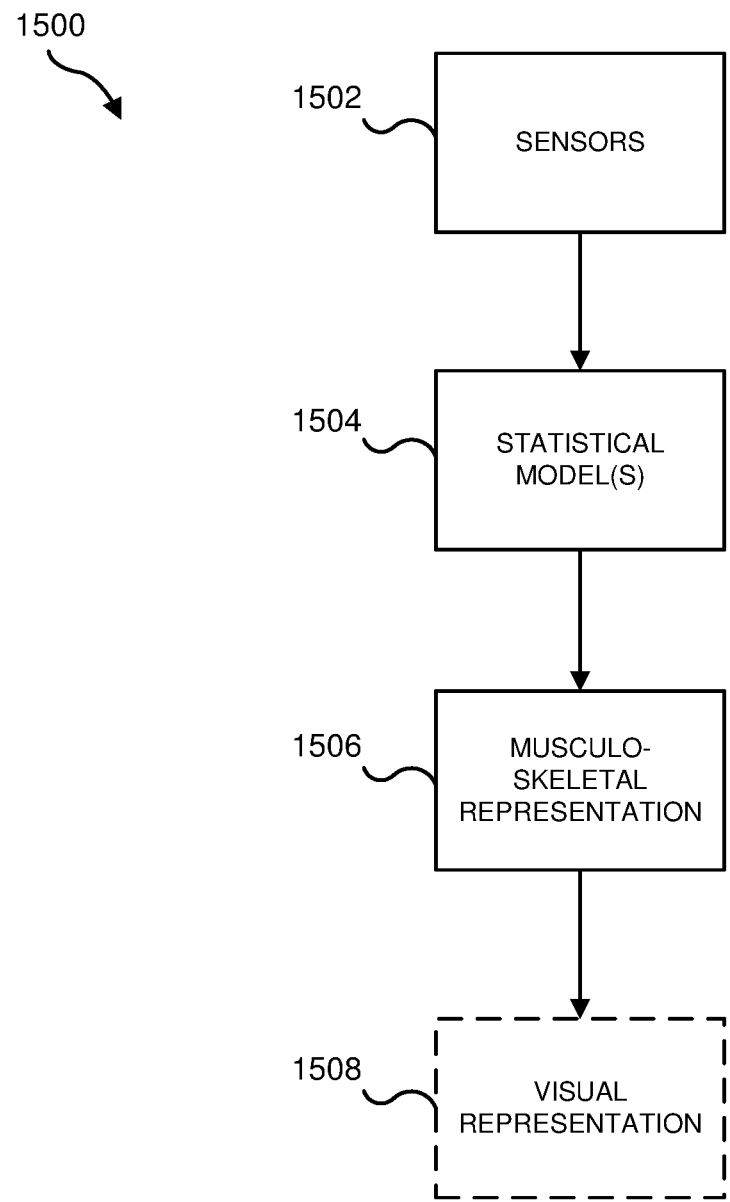
FIG. 15 is a schematic diagram of a computer-based system for generating a musculoskeletal representation based on neuromuscular sensor data in accordance with some embodiments of the technology described herein.

FIG. 15 illustrates a system 1500 in accordance with some embodiments. The system includes a plurality of sensors 1502 configured to record signals resulting from the movement of portions of a human body. Sensors 1502 may include autonomous sensors. As used herein, the term "autonomous sensors" may refer to sensors configured to measure the movement of body segments without requiring the use of external devices. In some embodiments, sensors 1502 may also include non-autonomous sensors in combination with autonomous sensors. As used herein, the term "non-autonomous sensors" may refer to sensors configured to measure the movement of body segments using external devices. Examples of external devices that include non-autonomous sensors include, but are not limited to, wearable (e.g. body-mounted) cameras, global positioning systems, and laser scanning systems.

Autonomous sensors may include a plurality of neuromuscular sensors configured to record signals arising from neuromuscular activity in skeletal muscle of a human body. The term "neuromuscular activity" as used herein may refer to neural activation of spinal motor neurons that innervate a muscle, muscle activation, muscle contraction, or any combination of the neural activation, muscle activation, and muscle contraction. Neuromuscular sensors may include one or more electromyography (EMG) sensors, one or more mechanomyography (MMG) sensors, one or more sonomyography (SMG) sensors, a combination of two or more types of EMG sensors, MMG sensors, and SMG sensors, and/or one or more sensors of any suitable type that are configured to detect neuromuscular signals. In some embodiments, the plurality of neuromuscular sensors may be used to sense muscular activity related to a movement of the part of the body controlled by muscles from which the neuromuscular sensors are arranged to sense the muscle activity. Spatial information (e.g., position and/or orientation information) and force information describing the movement may be predicted based on the sensed neuromuscular signals as the user moves over time.

Autonomous sensors may include one or more Inertial Measurement Units (IMUs), which measure a combination of physical aspects of motion, using, for example, an accelerometer, a gyroscope, a magnetometer, or any combination of one or more accelerometers, gyroscopes and magnetometers. In some embodiments, IMUs may be used to sense information about the movement of the part of the body on which the IMU is attached and information derived from the sensed data (e.g., position and/or orientation information) may be tracked as the user moves over time. For example, one or more IMUs may be used to track movements of portions of a user's body proximal to the user's torso relative to the sensor (e.g., arms, legs) as the user moves over time.

In embodiments that include at least one IMU and a plurality of neuromuscular sensors, the IMU(s) and neuromuscular sensors may be arranged to detect movement of different parts of the human body. For example, the IMU(s) may be arranged to detect movements of one or more body segments proximal to the torso (e.g., an upper arm), whereas the neuromuscular sensors may be arranged to detect movements of one or more body segments distal to the torso (e.g., a forearm or wrist). It should be appreciated, however, that autonomous sensors may be arranged in any suitable way, and embodiments of the technology described herein are not limited based on the particular sensor arrangement. For example, in some embodiments, at least one IMU and a plurality of neuromuscular sensors may be co-located on a body segment to track movements of body segment using different types of measurements. In one implementation described in more detail below, an IMU sensor and a plurality of EMG sensors are arranged on a wearable device configured to be worn around the lower arm or wrist of a user. In such an arrangement, the IMU sensor may be configured to track movement information (e.g., positioning and/or orientation over time) associated with one or more arm segments, to determine, for example whether the user has raised or lowered their arm, whereas the EMG sensors may be configured to determine movement information associated with wrist or hand segments to determine, for example, whether the user has an open or closed hand configuration.

Each of the autonomous sensors includes one or more sensing components configured to sense information about a user. In the case of IMUs, the sensing components may include one or more accelerometers, gyroscopes, magnetometers, or any combination thereof to measure characteristics of body motion, examples of which include, but are not limited to, acceleration, angular velocity, and sensed magnetic field around the body. In the case of neuromuscular sensors, the sensing components may include, but are not limited to, electrodes configured to detect electric potentials on the surface of the body (e.g., for EMG sensors) vibration sensors configured to measure skin surface vibrations (e.g., for MMG sensors), and acoustic sensing components configured to measure ultrasound signals (e.g., for SMG sensors) arising from muscle activity.

In some embodiments, the output of one or more of the sensing components may be processed using hardware signal processing circuitry (e.g., to perform amplification, filtering, and/or rectification). In other embodiments, at least some signal processing of the output of the sensing components may be performed in software. Thus, signal processing of autonomous signals recorded by the autonomous sensors may be performed in hardware, software, or by any suitable combination of hardware and software, as aspects of the technology described herein are not limited in this respect.

In some embodiments, the recorded sensor data may be processed to compute additional derived measurements that are then provided as input to a statistical model, as described in more detail below. For example, recorded signals from an IMU sensor may be processed to derive an orientation signal that specifies the orientation of a rigid body segment over time. Autonomous sensors may implement signal processing using components integrated with the sensing components, or at least a portion of the signal processing may be performed by one or more components in communication with, but not directly integrated with the sensing components of the autonomous sensors.

In some embodiments, at least some of the plurality of autonomous sensors are arranged as a portion of a wearable device configured to be worn on or around part of a user's body. For example, in one non-limiting example, an IMU sensor and a plurality of neuromuscular sensors are arranged circumferentially around an adjustable and/or elastic band such as a wristband or armband configured to be worn around a user's wrist or arm. Alternatively, at least some of the autonomous sensors may be arranged on a wearable patch configured to be affixed to a portion of the user's body. In some embodiments, multiple wearable devices, each having one or more IMUs and/or neuromuscular sensors included thereon, may be used to predict musculoskeletal position information for movements that involve multiple parts of the body.

In some embodiments, sensors 1502 only include a plurality of neuromuscular sensors (e.g., EMG sensors). In other embodiments, sensors 1502 include a plurality of neuromuscular sensors and at least one "auxiliary" sensor configured to continuously record a plurality of auxiliary signals. Examples of auxiliary sensors include, but are not limited to, other autonomous sensors such as IMU sensors, and non-autonomous sensors such as an imaging device (e.g., a camera), a radiation-based sensor for use with a radiation-generation device (e.g., a laser-scanning device), or other types of sensors such as a heart-rate monitor.

System 1500 also includes one or more computer processors (not shown in FIG. 15) programmed to communicate with sensors 1502. For example, signals recorded by one or more of the sensors may be provided to the processor(s), which may be programmed to execute one or more machine learning techniques that process signals output by the sensors 1502 to train one or more statistical models 1504, and the trained (or retrained) statistical model(s) 1504 may be stored for later use in generating a musculoskeletal representation 1506, as described in more detail below.

System 1500 also optionally includes a display controller configured to display a visual representation 1508 (e.g., of a hand). As discussed in more detail below, one or more computer processors may implement one or more trained statistical models configured to predict handstate information based, at least in part, on signals recorded by sensors 1502. The predicted handstate information is used to update the musculoskeletal representation 1506, which is then optionally used to render a visual representation 1508 based on the updated musculoskeletal representation incorporating the current handstate information. Real-time reconstruction of the current handstate and subsequent rendering of the visual representation reflecting the current handstate information in the musculoskeletal model may provide visual feedback to the user about the effectiveness of the trained statistical model to accurately represent an intended handstate. Not all embodiments of system 1500 include components configured to render a visual representation. For example, in some embodiments, handstate estimates output from the trained statistical model and a corresponding updated musculoskeletal representation are used to determine a state of a user's hand (e.g., in a virtual reality environment) even though a visual representation based on the updated musculoskeletal representation is not rendered (e.g., for interacting with virtual objects in a virtual environment in the absence of a virtually-rendered hand).

In some embodiments, a computer application configured to simulate a virtual reality environment may be instructed to display a visual representation of the user's hand. Positioning, movement, and/or forces applied by portions of the hand within the virtual reality environment may be displayed based on the output of the trained statistical model(s). The visual representation may be dynamically updated based on current reconstructed handstate information as continuous signals are recorded by the sensors 1502 and processed by the trained statistical model(s) 1504 to provide an updated computer-generated representation of the user's movement and/or exerted force that is updated in real-time.

As discussed above, some embodiments are directed to using a statistical model for predicting musculoskeletal information based on signals recorded from wearable autonomous sensors. The statistical model may be used to predict the musculoskeletal position information without having to place sensors on each segment of the rigid body that is to be represented in the computer-generated musculoskeletal representation. As discussed briefly above, the types of joints between segments in a multi-segment articulated rigid body model constrain movement of the rigid body. Additionally, different individuals tend to move in characteristic ways when performing a task that can be captured in statistical patterns of individual user behavior. At least some of these constraints on human body movement may be explicitly incorporated into statistical models used for prediction in accordance with some embodiments. Additionally or alternatively, the constraints may be learned by the statistical model through training based on ground truth data on the position and exerted forces of the hand and wrist in the context of recorded sensor data (e.g., EMG data). Constraints imposed in the construction of the statistical model are those set by anatomy and the physics of a user's body, while constraints derived from statistical patterns are those set by human behavior for one or more users from which sensor measurements are measured and used to train the statistical model. As described in more detail below, the constraints may comprise part of the statistical model itself being represented by information (e.g., connection weights between nodes) in the model.

As discussed above, some embodiments are directed to using a statistical model for predicting handstate information to enable the generation and/or real-time update of a computer-based musculoskeletal representation. The statistical model may be used to predict the handstate information based on IMU signals, neuromuscular signals (e.g., EMG, MMG, and SMG signals), external device signals (e.g., camera or laser-scanning signals), or a combination of IMU signals, neuromuscular signals, and external device signals detected as a user performs one or more movements.

Figure 16:
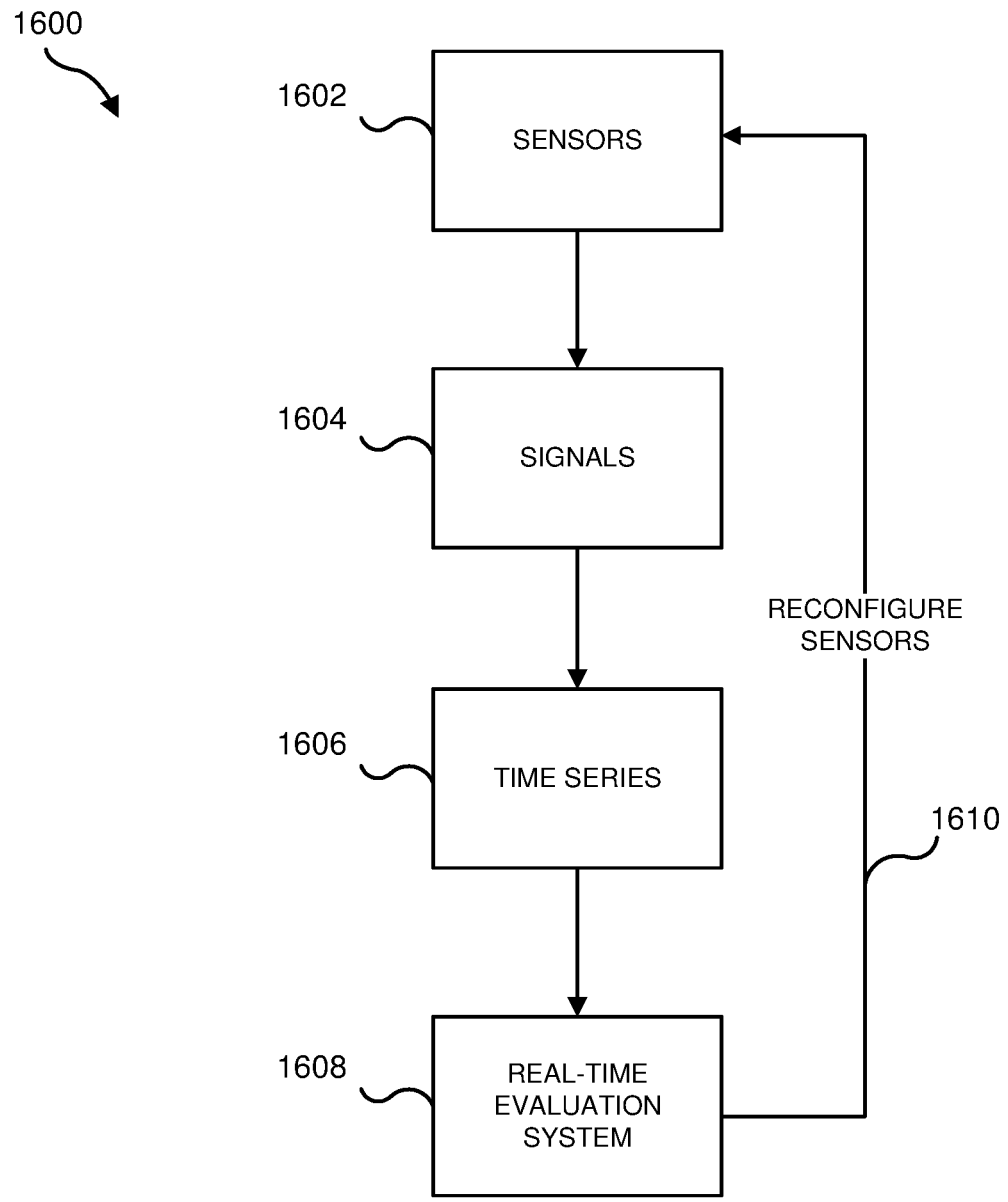
FIG. 16 is a diagram of a computer-based system for configuring neuromuscular sensors based on neuromuscular sensor data.

FIG. 16 shows a computer-based system 1600 for configuring neuromuscular sensors based on neuromuscular sensor data in accordance with some embodiments. The system includes a plurality of sensors 1602 configured to record signals resulting from the movement of portions of a human body. Sensors 1602 may include autonomous sensors.

System 1600 also includes one or more computer processors (not shown in FIG. 16) programmed to communicate with sensors 1602. For example, signals 1604 recorded by one or more of the sensors 1602 may be provided to the processor(s), which may be programmed to identify a time series with values acquired via sensors 1602. The processor(s), as a part of a real-time system, may evaluate the quality of signals 1604 received from, e.g., a single sensor or a pair of differential sensors using the methods described above.

The term "differential sensors," as used herein, may refer to any pair or set of sensors whose signals are compared and/or combined (e.g., by subtracting one from another) to produce a composite signal (e.g., with the end of reducing or eliminating noise from the signals). For example, in the case of electrodes used as neuromuscular sensors, the raw voltage signal from an electrode in the absence of relevant neuromuscular activity may typically represent noise (e.g., ambient electromagnetic noise from the environment and/or intrinsic amplifier noise). On the assumption that two electrodes will experience the same noise, by subtracting the signal of an electrode only observing noise from the signal of an electrode whose signal represents relevant activity plus noise, the relevant signal may be isolated. However, as described herein, in some cases sensors may experience noise unevenly, and systems and methods described herein may dynamically configure differential sensor pairings to improve the resultant signal.

As discussed above, a real-time system may evaluate, based on received time series data, the performance of a sensor and/or a pair of differential sensors. For example, the real-time system can determine if a particular electrode in a pair of differential electrodes is not in contact with the user's skin. An electrode that is not in contact with the user's skin can generate signals characterized by out-of-range amplitude and frequency discontinuities. The real-time system can reconfigure the array of electrodes to replace or deactivate the channel of the electrode that is not in contact with the user's skin with another electrode determined to be in contact with the user's skin. Thus, the dynamically configurable arrangement of electrodes ensures that only electrodes in contact with the user skin are used to compute measurements.

In some instances, the real-time system configures multiple pairs of sensors in the arrangement, each pair of sensors being used to compute differential measurements. Sensors in each pair do not need to be located at equal distances. Differently stated, sensors in a first pair of sensors can be separated by a first distance, while sensors in a second pair of electrodes can be separated by a second distance, wherein the first distance is different from the second distance. Configuring pairs of sensors, where the sensors in one pair are separated by a different distance than the sensors in another pair results in a flexible and adaptable system capable of retrieving differential measurements from pairs of sensors known to be better predictors of, for example, an amount of applied force, gestures, and/or poses (collectively "interactions") performed by a user. Moreover, this flexible configuration enables the acquisition of differential measurements from electrodes paired according to the direction of a signal propagation (e.g., in a line down the arm or wrist), horizontally across the arm or wrist, or diagonally (both down and horizontally across the arm or wrist). Accordingly, the armband system can be configured to reduce and/or correct motion artifacts by selecting specific electrodes identified as motion resilient when the real-time system detects the infiltration of motion artifacts in the acquired signals.

In some implementations, the real-time system can activate sensors positioned at specific areas of the arm or wrist depending on an activity being performed by the user. For example, when the user engages in a typing task, the real-time system can determine such activity and accordingly can steer the sampling density to the underside arm nerves by, for example, activating and pairing sensors located in such region. For another example, the sampling density can focus on regions of the arm associated with the movement of a finger (e.g., for mission critical discrete controls) or configured in a distributed full arm or wrist sampling configuration when predictions are made regarding the user's handstate.

In some implementations, the configurable array of sensors can reduce the number of channels in the armband system that remain active at a given time. For example, the real-time system can determine that, for a specific task, predictions of interactions performed by a user can be computed from signals received from a first set of sensors, while the signals received from a second set of sensors are discarded or ignored. In such a case, the real-time system can activate the first set of sensors and deactivate the second set of sensors resulting in a more efficient use of computational resources.

In some examples, the systems and methods described herein may dynamically configure sensors in a way that is personalized to the particular user. For example, the shape of the user's arm or wrist, the fit of the wearable device on the user, the characteristics of the neuromuscular signals received from the user, surface qualities of the user's skin, and/or the hairiness of the user's arm may impact how suited various sensors are to producing accurate and/or useful signals (e.g., for a system that converts neuromuscular signals into musculoskeletal representations). In some examples, systems described herein may observe and evaluate sensor performance and quality during specific user-performed tasks. By determining that certain sensors provide more reliable performance during certain tasks for a given user, the systems and methods described herein may dynamically adjust the configurable array of sensors to use data from pairs of differential sensors that provide signals most representative of the user's activity for those tasks. Thus, for example, an XR system that consumes the neuromuscular signals to produce musculoskeletal representations of the user's hand may provide high-level information about activities that the user is engaged in (e.g., typing, interacting with particular types of virtual objects, etc.) or predicted to be engaging in so that systems described herein may adjust the configurable array of sensors according to a stored user profile.

In some examples, systems described herein may prospectively adjust the configurable array of sensors (e.g., based on information received about an application that the user has initiated, an input mode that the user has selected, a task that the user is predicted to start performing). Additionally or alternatively, systems described herein may adjust the configurable array of sensors in response to observed performance issues and/or errors (e.g., detecting that an electrode has come out of contact with the user's skin). In some examples, systems described herein may evaluate sensor performance before providing sensor data to subsystems that consume the sensor data (e.g., an inferential model that produces a musculoskeletal representation of the user's hand based on the neuromuscular sensor data). Additionally or alternatively, systems described herein may partly evaluate sensor performance based on performance issues observed by the subsystems that consume the sensor data. For example, an inferential model (and/or associated subsystems for interpreting neuromuscular data) may produce a musculoskeletal representation with a large expected error term. While systems described herein may attribute some of the error to the inferential model, in some embodiments systems described herein may attribute some of the error to sensor performance. These systems may therefore backpropagate the error to the sensor array, and a real-time system may reconfigure the sensor array at least partly in response to the backpropagated error.

As detailed above, the computing devices and systems described and/or illustrated herein broadly represent any type or form of computing device or system capable of executing computer-readable instructions, such as those contained within the modules described herein. In their most basic configuration, these computing device(s) may each include at least one memory device and at least one physical processor.

In some examples, the term "memory device" generally refers to any type or form of volatile or non-volatile storage device or medium capable of storing data and/or computer-readable instructions. In one example, a memory device may store, load, and/or maintain one or more of the modules described herein. Examples of memory devices include, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In some examples, the term "physical processor" generally refers to any type or form of hardware-implemented processing unit capable of interpreting and/or executing computer-readable instructions. In one example, a physical processor may access and/or modify one or more modules stored in the above-described memory device. Examples of physical processors include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the modules described and/or illustrated herein may represent portions of a single module or application. In addition, in certain embodiments one or more of these modules may represent one or more software applications or programs that, when executed by a computing device, may cause the computing device to perform one or more tasks. For example, one or more of the modules described and/or illustrated herein may represent modules stored and configured to run on one or more of the computing devices or systems described and/or illustrated herein. One or more of these modules may also represent all or portions of one or more special-purpose computers configured to perform one or more tasks.

In addition, one or more of the modules described herein may transform data, physical devices, and/or representations of physical devices from one form to another. For example, one or more of the modules recited herein may receive an output signal of an amplifier to be transformed, transform the output signal into a power spectral density, output a result of the transformation to an impedance-measuring system, use the result of the transformation to estimate an interface impedance, and/or store the result of the transformation to physical memory. Additionally or alternatively, one or more of the modules recited herein may transform a processor, volatile memory, non-volatile memory, and/or any other portion of a physical computing device from one form to another by executing on the computing device, storing data on the computing device, and/or otherwise interacting with the computing device.

In some embodiments, the term "computer-readable medium" generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed. The various exemplary methods described and/or illustrated herein may also omit one or more of the steps described or illustrated herein or include additional steps in addition to those disclosed.

The preceding description has been provided to enable others skilled in the art to best utilize various aspects of the exemplary embodiments disclosed herein. This exemplary description is not intended to be exhaustive or to be limited to any precise form disclosed. Many modifications and variations are possible without departing from the spirit and scope of the present disclosure. The embodiments disclosed herein should be considered in all respects illustrative and not restrictive. Reference should be made to the appended claims and their equivalents in determining the scope of the present disclosure.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and have the same meaning as the word "comprising."

What is claimed is:

1. A wearable device for detecting neuromuscular activity, comprising:
    at least two dry electrodes configured to electrically couple to an external body surface of a wearer of the wearable device;
    signal-amplifying circuitry configured to amplify electrical signals from the at least two dry electrodes; and
    impedance-measuring circuitry that:
        estimates an interface impedance of at least one of the two dry electrodes based on a spectral density of an output signal of the signal-amplifying circuitry and a predetermined intrinsic current noise of the signal-amplifying circuitry; and
        performing an operation based at least in part on the estimated interface impedance.

2. The wearable device of claim 1, wherein the electrically coupling includes physical contact between the at least two dry electrodes and the external body surface of the wearer.

3. The wearable device of claim 1, wherein the electrically coupling includes capacitive coupling between the at least two dry electrodes and the external body surface of the wearer.

4. The wearable device of claim 1, wherein the impedance-measuring circuitry estimates the interface impedance by:
    calculating a power spectral density of the output signal;
    calculating, using the power spectral density, a noise power of the output signal over a predetermined frequency band; and
    estimating the interface impedance based on the noise power.

5. The wearable device of claim 1, wherein the signal-amplifying circuitry comprises a differential amplifier.

6. The wearable device of claim 1 wherein:
    the at least two dry electrodes comprise a pair of dry electrodes; and
    the electrical signals comprise differential signals received by the pair of dry electrodes.

7. The wearable device of claim 6, wherein the at least two dry electrodes further comprise a dry ground electrode configured to receive ground signals from which the differential signals are referenced.

8. A non-transitory computer-readable storage medium, comprising instructions that, when executed by a wearable device that includes (i) at least two dry electrodes that are electrically coupled to an external body surface of a wearer of the wearable device, (ii) signal-amplifying circuitry, and (iii) impedance-measuring circuitry, cause operations for:
   amplifying, using the signal-amplifying circuitry, electrical signals from the at least two dry electrodes; and
   using the impedance-measuring circuitry:
      estimating an interface impedance of at least one of the two dry electrodes based on a spectral density of an output signal of the signal-amplifying circuitry and a predetermined intrinsic current noise of the signal-amplifying circuitry; and
      performing an operation based at least in part on the estimated interface impedance.

9. The non-transitory computer-readable storage medium of claim 8, wherein the electrically coupling includes physical contact between the at least two dry electrodes and the external body surface of the wearer.

10. The non-transitory computer-readable storage medium of claim 8, wherein the electrically coupling includes capacitive coupling between the at least two dry electrodes and the external body surface of the wearer.

11. The non-transitory computer-readable storage medium of claim 8, further comprising instructions for:
   using the impedance-measuring circuitry:
      calculating a power spectral density of the output signal;
      calculating, using the power spectral density, a noise power of the output signal over a predetermined frequency band; and
      estimating the interface impedance based on the noise power.

12. The non-transitory computer-readable storage medium of claim 8, wherein the signal-amplifying circuitry comprises a differential amplifier.

13. The non-transitory computer-readable storage medium of claim 8, wherein:
   the at least two dry electrodes comprise a pair of dry electrodes; and
   the electrical signals comprise differential signals received by the pair of dry electrodes.

14. The non-transitory computer-readable storage medium of claim 13, wherein the at least two dry electrodes further comprise a dry ground electrode configured to receive ground signals from which the differential signals are referenced.

15. A method, comprising:
   at a wearable device comprising (i) at least two dry electrodes that are electrically coupled to an external body surface of a wearer of the wearable device, (ii) signal-amplifying circuitry, and (iii) impedance-measuring circuitry, (iv) one or more processors, and (v) memory, comprising instructions which, when executed by the one or more processors, cause operations comprising:
      amplifying, using the signal-amplifying circuitry, electrical signals from the at least two dry electrodes; and
      using the impedance-measuring circuitry:
         estimating an interface impedance of at least one of the two dry electrodes based on a spectral density of an output signal of the signal-amplifying circuitry and a predetermined intrinsic current noise of the signal-amplifying circuitry; and
         performing an operation based at least in part on the estimated interface impedance.

16. The method of claim 15, wherein the electrically coupling includes physical contact between the at least two dry electrodes and the external body surface of the wearer.

17. The method of claim 15, wherein the memory further comprises instructions for:
   using the impedance-measuring circuitry:
      calculating a power spectral density of the output signal;
      calculating, using the power spectral density, a noise power of the output signal over a predetermined frequency band; and
      estimating the interface impedance based on the noise power.

18. The method of claim 15, wherein the signal-amplifying circuitry comprises a differential amplifier.

19. The method of claim 15, wherein:
   the at least two dry electrodes comprise a pair of dry electrodes; and
   the electrical signals comprise differential signals received by the pair of dry electrodes.

20. The method of claim 19, wherein the at least two dry electrodes further comprise a dry ground electrode configured to receive ground signals from which the differential signals are referenced.

* * * * *